United States Patent [19]
Nunn et al.

[11] Patent Number: 5,387,409
[45] Date of Patent: Feb. 7, 1995

[54] BORONIC ACID ADDUCTS OF RHENIUM DIOXIME AND TECHNETIUM-99M DIOXIME COMPLEXES CONTAINING A BIOCHEMICALLY ACTIVE GROUP

[75] Inventors: Adrian D. Nunn, Ringoes; Karen E. Linder, Kingston, both of N.J.; Silvia Jurisson, Columbia, Mo.; William C. Eckelman, Bethesda, Md.

[73] Assignee: Bracco International B.V., Amsterdam, Netherlands

[21] Appl. No.: 818,705

[22] Filed: Jan. 7, 1992

Related U.S. Application Data

[63] Continuation-in-part of Ser. No. 466,884, Jan. 18, 1990, abandoned.

[51] Int. Cl.$^6$ ...................... A61K 49/02; A61K 43/00
[52] U.S. Cl. .................................. 424/1.45; 424/1.65; 424/1.69; 424/1.73; 534/10; 534/14
[58] Field of Search ...................... 424/1.1, 1.45, 1.53, 424/1.65, 1.69, 1.73; 534/10, 14

[56] References Cited

U.S. PATENT DOCUMENTS

| | | |
|---|---|---|
| 4,431,627 | 2/1984 | Eckelman et al. |
| 4,705,849 | 11/1987 | Nunn et al. ............................. 534/14 |
| 4,871,836 | 10/1989 | Francesconi et al. ................. 534/10 |

FOREIGN PATENT DOCUMENTS

| | | |
|---|---|---|
| 89/102182.5 | 10/1990 | China. |
| 0199260 | 10/1986 | European Pat. Off.. |
| 0311891 | 4/1989 | European Pat. Off.. |

OTHER PUBLICATIONS

Chemical Abstracts, Abstract No. 59625V, vol. 84, p. 545, 1976.
Chemical Abstracts, Abstract No. 11735q, vol. 70, p. 293, 1969.
Fowler et al., *Int. J. Appl. Radiat. Isot.*, 1986, 27, pp. 663–668, "2-deoxy-2[$^{18}$F]fluoro-D-glucose for metabolic studies: current status".
Winchell et al., *J. Nucl. Med.*, 1980, 21, pp. 940–946 "Development of I-123-Labeled Amines for Brain Studies: Localization of I-123 Iodophenylalkyl Amines in Rat Brain".
Winchell et al., *J. Nucl. Med.*, 1980, 21, pp. 947–952, "N-Isopropyl-[$^{123}$I]p-Iodoamphetamine: Single-Pass Brain Uptake and Washout; Binding to Brain Synaptosomes and Localization in Dog and Monkey Brain".
van der Wall et al., *Eur. J. Nucl. Med.*, 1986, 12, pp. 511–515, "Myocardial Imaging with Radiolabeled Free Fatty Acids: Applications and Limitations".
Jones et al., *J. Nucl. Med.*, 1988, 29(5), p. 935 "Synthesis of a Novel [Tc99m]-Diaminodithiol-Fatty Acid (TcN$_2$S$_2$FA) Complex and its Evaluation as a Myocardial Imaging Agent".
Jagoda et al., *J. Nucl. Med.*, 1984, 25, pp. 472–477, "[$^{125}$I]-17-Iodovinyl-11-Methoxyestradiol: In vivo and In vitro Properties of a High Affinity Estrogen-Receptor Radiopharmaceutical".
Gibson et al., *Biochem. Pharm.*, vol. 32, No. 12, pp. 1851–1856, 1983, "Differences in Affinities for Muscarinic Acetylcholine Receptor Antagonists for Brain and Heart Receptors".
Gibson et al., *J. Nucl. Med.*, vol. 25, No. 2, pp. 214–222, 1984, "The Characteristics of I-125 4-IQNB and H-3QNB In Vivo and In Vitro".
Martin et al., *J. Nucl. Med.*, vol. 30, No. 2, 194–201 (1989) "Enhanced Binding of the Hypoxic Cell Marker [$^3$H] Fluoromisonidazole".
Hoffman et al., *Stroke*, 18, p. 168 (1987) "Binding of the Hypoxic Tracer [H-3] Misonidazole in Cerebral Ischemia".
Koh et al., *J. Nucl. Med.*, p. 789, 30, 1989 "Hypoxia Imaging of Tumors Using [F-18] Fluoromisonidazole".
Kedderis et al., *Drug Metabolism Reviews*, 19(1), pp. 33–62 (1988) "The Metabolic Activation of Nitro-Heterocyclic Therapeutic Agents".
Adams, et al., *Biochem. Pharmacology*, vol. 35, No. 1, pp. 71–76 (1986) "Hypoxia Mediated Nitro-Heterocyclic Drugs in the Radio- and Chemotherapy of Cancer".
Brown et al., *Rad. Research*, 90, pp. 98–108 (1982) "Structure-Activity Relationships of 1-Substituted 2-Nitroimidazoles: Effect of Partition Coefficient and Sidechain Hydroxyl Groups on Radiosensitization in vitro".
Adams et al., *Int. J. Radiat. Biol.*, vol. 35, No. 2, pp. 133–150 (1979) "Structure-Activity Relationships in the Development of Hypoxic Cell Radiosensitizers".
Adams et al., *Int. J. Radiat. Biol.*, vol. 38, No. 6, 613–626 (1980) "Structure-Activity Relationships in the Development of Hypoxic Cell Radiosensitizers".
Kabalka et al., *Nucl. Med. Biol.*, 1989, 16(4), pp. 359–360.
Y. Lixi et al., *Journal of Medical Colleges of PLA*, 2(3): pp. 265–269, 1987, "Synthesis of Metronidazole Derivative and its Distribution in Sarcoma 180 Bearing Mice".

Primary Examiner—Robert L. Stoll
Assistant Examiner—John M. Covert

[57] ABSTRACT

Boronic acid adducts of technetium-99m and radioactive rhenium dioxime complexes, each of which include biochemically active groups, are useful as diagnostic and therapeutic agents, respectively.

51 Claims, No Drawings

BORONIC ACID ADDUCTS OF RHENIUM DIOXIME AND TECHNETIUM-99M DIOXIME COMPLEXES CONTAINING A BIOCHEMICALLY ACTIVE GROUP

This is a continuation-in-part application of U.S. Ser. No. 466,884, filed Jan. 18, 1990, now abandoned.

BACKGROUND OF THE INVENTION

Radiolabeled biochemically active groups are of increasing interest in the field of diagnostic imaging. Essentially, a biochemically active group is a metabolic substrate or inhibitor or a molecule with an affinity for a specific receptor. Knowledge of certain properties, such as receptor binding or metabolism, involving various biochemically active groups suggest, at least in theory, that radiolabeled versions of such groups may be useful in imaging the function and/or condition of a specific organ, rather than merely the blood flow to that organ. An effective complex is one wherein the radionuclide and biochemically active group are stably bound to each other and further, wherein the complex behaves, or is "taken up" substantially as the free biochemically active group would behave.

Numerous attempts to prepare effective complexes of this nature have been reported. For example, Fowler et al. (*Int. J. Appl. Radiat. Isot.*, 1986, 27, p. 663–8, "2-deoxy-2[$^{18}$F]fluoro-D-glucose for metabolic studies: current status") have investigated the radiolabeling of the metabolic substrate, deoxyglucose, with $^{18}$F for use in diagnostic imaging of the brain. Brain and lung imaging has also been attempted by Winchell et al. (*J. Nucl. Med.*, 1980, 21, p. 940–6, "Development of I-123-Labeled Amines for Brain Studies: Localization of I-123 Iodophenylalkyl Amines in Rat Brain" and *J. Nucl. Med.*, 1980, 21, p. 947–52, "N-Isopropyl-[$^{123}$I]p-Iodoamphetamine: Single-Pass Brain Uptake and Washout; Binding to Brain Synaptosomes; and Localization in Dog and Monkey Brain") who report radiolabeling of amphetamines, known to interact with specific receptors, with $^{123}$I. The radio-iodinated amphetamine known as "Spectamine" is currently marketed for brain imaging.

Free fatty acids are primary substrates of the normally perfused myocardium and, as such, are viewed as potentially useful in studying free fatty acid metabolism via the beta-oxidation pathway. Accordingly, van der Wall et al. (*Eur. J. Nucl. Med.*, 1986, 12, p. S11–S15, "Myocardial imaging with radiolabeled free fatty acids: Applications and limitations") have studied free fatty acid labeled with positron emitting isotopes, e.g., $^{11}$C, $^{13}$N and $^{15}$O, as well as with the gamma-emitting isotope $^{123}$I. Additionally, Jones et al. (*J. Nucl. Med.*, 1988, 29(5), p. 935, "Synthesis of a Novel [Tc99m]-Diaminodithiol-Fatty Acid (TcN$_2$S$_2$FA) Complex and Its Evaluation as a Myocardial Imaging Agent") have disclosed attempts to image normal myocardium utilizing fatty acids with technetium-99m ($^{99}$mTc).

The discovery of specific estrogen receptors in breast carcinoma has led to work in the radiolabeling of various steroids, e.g., estrogens or derivatives thereof, e.g., estradiols. It is believed that a radiolabeled estrogen may be able to indicate receptor levels and help determine types and levels of therapy for breast carcinoma. In this regard, Jagoda et al., (*J. Nucl. Med.*, 1984, 25, p. 472–7, "[$^{125}$I]-17-Iodovinyl 11-Methoxyestradiol: *In vivo* and *In vitro* Properties of a High Affinity Estrogen-Receptor Radiopharmaceutical") have studied $^{125}$I labeled methoxy estradiol for such diagnostic uses.

Gibson et al. (*Biochem Pharm.*, Vol. 32, No. 12, p. 1851–56, 1983, "Differences in Affinities of Muscarinic Acetylcholine Receptor Antagonists for Brain and Heart Receptors" and *J. Nucl. Med.*, Vol. 25, No. 2, p. 214–222, February 1984, "The Characteristics of I-125 4-IQNB and H-3QNB In vivo and In vitro") have studied the substrates for muscarinic receptors, e.g. 3-quinuclidinyl benzilate (QNB) and derivatives thereof, radiolabeled with $^{125}$I and $^{3}$H in heart and brain tissue.

As reported by Martin et al. ("Enhanced Binding of the Hypoxic Cell Marker [$^3$H] Fluoromisonidazole", *J. Nucl. Med.*, Vol 30, No. 2, 194–201 (1989)) and Hoffman et al. ("Binding of the Hypoxic Tracer [H-3] Misonidazole in Cerebral Ischemia", *Stroke*, 1987, 18, 168), hypoxia-mediated nitro-heterocyclic groups (e.g., nitroimidazoles, and derivatives thereof) are known to be retained in tissue in the body which is hypoxic, i.e., deficient in oxygen. Hypoxic tissue in the brain or heart typically follows ischemic episodes produced by, for example, arterial occlusions or by a combination of increased demand and insufficient flow. Additionally, Koh et al., (*J. Nucl. Med.*, 1989, 30, p. 789, "Hypoxia Imaging of Tumors Using [F-18]Fluoromisonidazole") have attempted diagnostic imaging of tumors using a nitroimidazole radio labeled with $^{18}$F.

The above-mentioned attempts at diagnostic imaging with various radiolabeled biochemically active groups have provided less than ideal results to this point. For example, the positron emitting isotopes are cyclotron produced and require expensive equipment for imaging which is not widely available. Similarly, $^{123}$I has a thirteen hour half life and is expensive to produce. Further, the $^{99}$mTc complexes with fatty acids have not demonstrated the characteristics of the free fatty acids in myocardial uptake. Finally, the tritium labeled nitroimidazoles are beta-emitting nuclides useful only for autoradiographic studies and not suitable for diagnostic imaging.

Radiolabeled complexes of biochemically active groups which retain the biochemical behavior and affinity of such groups, and which are labeled with a suitable, easy-to-use radionuclide would be a useful addition to the art.

BRIEF DESCRIPTION OF THE INVENTION

In accordance with the present invention, boronic acid adducts of rhenium dioxime and technetium dioxime complexes are bonded to a biochemically active group and are useful, for example, as diagnostic imaging agents in the case of technetium radionuclides and as agents for radiotherapy in the case of rhenium radionuclides. These novel complexes are represented by the formula

$$MX(Y_3)Z, \quad\quad\quad I$$

wherein M is an isotope of technetium or rhenium. Unless otherwise noted, rhenium includes $^{186}$Re and $^{188}$Re radionuclides, including mixtures thereof, and may also include amounts of $^{185}$Re and $^{187}$Re. Unless otherwise noted, technetium includes $^{94}$Tc, $^{96}$Tc and $^{99}$mTc including mixtures, and may also include amounts of $^{94m}$Tc and $^{95}$Tc. In formula I, and throughout the specification, the symbols are as defined below X is an anion;

Y is a vicinal dioxime having the formula

or a pharmaceutically acceptable salt thereof, and $R_1$ and $R_2$ are each independently hydrogen, halogen, alkyl, aryl, amino or a 5- or 6-membered nitrogen or oxygen containing heterocycle, or together $R_1$ and $R_2$ are $-(CR_8R_9)_n-$ wherein n is 3, 4, 5 or 6 and $R_8$ and $R_9$ are each independently hydrogen or alkyl;

Z is a boron derivative having the formula

wherein $R_3$ is, or contains, a biochemically active group, and wherein $(A_1)_p$ is absent when p=0 or is a spacer group when p is $\geq 1$.

As shown, in the case where the biochemically active group may be inhibited in its action by the close proximity of the remainder of the complex, it (the biochemically active group) can be bound to the complex via the spacer or linking group, $(A_1)_p$. This spacer group can be any chemical moiety which can serve to physically distance, or otherwise isolate, the biochemically active group at $R_3$ from the rest of the complex of formula I. For example, in the spacer group, wherein p is one, $A_1$, or the various $A_1$ units in forming a straight or branched chain if p>1, are independently selected from $-CH_2-$, $-CHR_4-$, $-CR_4R_5-$, $-CH=CH=$, $-CH=CR_4-$, $-CR_4=CR_5-$, $-C\equiv C-$, cycloalkyl, cycloalkenyl, aryl, heterocyclo, oxygen, sulfur,

$-NH-$, $-HC=N-$, $-CR_4=N-$, $-NR_4-$, $-CS-$; wherein $R_4$ and $R_5$ are independently selected from alkyl, alkenyl, alkoxy, aryl, 5- or 6-membered nitrogen- or oxygen-containing heterocycle, halogen, hydroxy or hydroxyalkyl.

In considering the various spacer groups known in the art, it is understood that p could be any convenient value depending upon the design choices for the desired complex. Preferably, p is $\leq 100$ and most preferably $p \leq 20$.

Listed below are definitions of the terms used to describe the complexes of this invention. These definitions apply to the terms as they are used throughout the specification (unless they are otherwise limited in specific instances) either individually or as part of a larger group.

The terms "alkyl", "alkenyl" and "alkoxy" refer to both straight and branched chain groups. Those groups having 1 to 10 carbon atoms are preferred.

The term "aryl" refers to phenyl and substituted phenyl. Preferred are phenyl and phenyl substituted with 1, 2 or 3 alkyl, haloalkyl, aminoalkyl, alkylaminoalkyl, dialkylaminoalkyl, alkoxy, alkoxyalkyl, halogen, amino, hydroxy, or formyl groups.

The terms "halide", "halo" and "halogen" refer to fluorine, chlorine, bromine and iodine.

The expression "5- or 6-membered nitrogen containing heterocycle" refers to all 5- and 6-membered rings containing at least one nitrogen atom. Exemplary aliphatic groups are dehydro derivatives of a compound having the formula

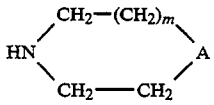

wherein m is 0 or 1 and A is $-O-$, $-N-R_6$, $-S-$ or $-CH-R_6$ wherein $R_6$ is hydrogen, alkyl, aryl or arylalkyl. Such groups include pyrrolidinyl, piperidinyl, morpholinyl, piperazinyl, 4-alkylpiperazinyl, 4-alkylpiperidinyl, and 3-alkylpyrrolidinyl groups. Also included within the expression "5- or 6-membered nitrogen containing heterocycle" are aromatic groups. Exemplary aromatic groups are pyrrolyl, imidazolyl, oxazolyl, pyrazolyl, pyridinyl, and pyrimidinyl groups. The above groups can be linked via a hetero atom or a carbon atom.

The expression "5- or 6-membered nitrogen or oxygen containing heterocycle" refers to all 5- and 6-membered rings containing at least one nitrogen or oxygen atom. Exemplary groups are those described above under the definition of the expression "5- or 6-membered nitrogen containing heterocycle". Additional exemplary groups are 1,4-dioxanyl and furanyl.

DETAILED DESCRIPTION OF THE INVENTION

For those complexes of the present invention wherein M is rhenium, the biochemically active group is bound to complexes as defined in U.S. Pat. No. 4,871,836 issued Oct. 3, 1989. For those complexes of formula I where M is one of the technetium radionuclides, the biochemically active group is bound to a complex as defined in U.S. Pat. No. 4,705,849, issued Nov. 10, 1987.

The present invention provides complexes comprising radiolabeled biochemically active groups. A biochemically active group suitable for use in the present invention is any metabolic substrate or inhibitor, or a molecule with an affinity for a specific receptor. It is understood that for the purpose of this invention the category of biochemically active groups which are molecules with an affinity for specific receptor sites is limited to those groups capable of being incorporated into the complexes of formula I by the methodology described hereinafter.

Examples of suitable biochemically active groups include, but are not limited to, hypoxia-mediated nitroheterocyclic groups, amphetamines, steroids (such as an estrogen or estradiol), sugars (e.g. glucose derivatives), fatty acids, barbiturates, sulfonamides, monoamine oxidase substrates and inhibitors, antihypertensives, substrates for muscarinic receptors (e.g., 3-quinuclidinyl benzilate), substrates for dopamine receptors (e.g., spiperone) and substrates for benzodiazepine receptors.

Complexes of the present invention have not been heretofore disclosed and are useful in that they utilize properties, e.g., receptor binding, metabolism, etc., of a particular biochemically active group to provide imaging or treatment of a particular site. The complexes of the present invention wherein M is $^{99m}Tc$ provide highly effective, relatively easy to use diagnostic imaging products which are characterized by a covalent bond between the radionuclide complex and the biochemically active group while substantially retaining the uptake properties of the free biochemical group. It can be appreciated that typical examples of diagnostic uses for the complexes of the present invention when M is $^{99m}Tc$ include, but are not limited to, imaging of hypoxic tissue, e.g., in the heart, brain, lungs or in tumors when the biochemically active group is a nitro-heterocyclic group trapped by hypoxia-mediated reduction of the nitro moiety (hereinafter referred to as "hypoxia-mediated nitro-heterocyclic group"); imaging of the brain and lungs when the biochemically active group is a lipophilic amine-containing compound, e.g. an amphetamine; imaging of the brain, heart or tumors when the biochemically active group is a sugar (e.g., a glucose derivative); imaging of the heart when the biochemically active group is a fatty acid; and imaging of steroid receptor sites when the biochemically active group is asteroid (e.g., an estrogen for imaging breast carcinoma).

Additionally, the present invention provides stably bound complexes when M is Re for radiotherapeutic indications. For example, the above-mentioned U.S. Pat. No. 4,871,836 issued Oct. 3, 1989 describes Re complexes for radiotherapy. Re complexes of the present invention which include estradiols can be used in the treatment of breast carcinoma. Also, to the extent that hypoxic tissue is known to be present in tumors, Re complexes of the present invention wherein the biochemically active group is a hypoxia-mediated nitro-heterocyclic group are suitable for radiotherapy. The compounds of this invention when M is Re for use in radiotherapy can be injected into humans and concentrate at the desired site. This allows for the targeting of radionuclides to the desired sites with great specificity. It is understood, however, that radiotherapy will only be possible in those areas where a sufficient quantity of interacting sites (i.e., estrogen receptors or hypoxic tissue) are present so as to provide therapeutic levels of rhenium to the area needing treatment.

Examples of hypoxia-mediated nitro-heterocyclic groups, (i.e., nitro-heterocyclic groups trapped by hypoxia-mediated reduction of the nitro moiety), in addition to the Koh et al. and Hoffman et al. references above, include those described in "The Metabolic Activation of Nitro-Heterocyclic Therapeutic Agents", G. L. Kedderis et al., Drug Metabolism Reviews, 19(1), p. 33–62 (1988), "Hypoxia Mediated Nitro-Heterocyclic Drugs in the Radio- and Chemotherapy of Cancer", G. E. Adams, et al., Biochem. Pharmacology, Vol. 35, No. 1, pages 71–76 (1986); "Structure-Activity Relationships of 1-Substituted 2-Nitroimidazoles: Effect of Partition Coefficient and Sidechain Hydroxyl Groups on Radiosensitization In vitro", D. M. Brown et al., Rad. Research, 90, 98–108 (1982); "Structure-Activity Relationships in the Development of Hypoxic Cell Radiosensitizers", G. E. Adams et al., Int. J. Radiat. Biol., Vol. 35, No. 2, 133–150 (1979); and "Structure-Activity Relationships in the Development of Hypoxic Cell Radiosensitizers", G. E. Adams et al., Int. J. Radiat. Biol., Vol. 38, No. 6, 613–626 (1980). These all disclose various nitro-heterocyclic compounds suitable for use at $R_3$ in the complexes of the present invention and are incorporated herein by reference. These compounds comprise a nitro-heterocyclic group which may include a sidechain, $A_1$, which can serve as the spacer group linking the nitro-heterocyclic portion to the boron atom and the rest of the complex of formula I of this invention. When the biochemically active group is a hypoxia-mediated nitro-heterocyclic group, the spacer-$R_3$ portion of the complex can be represented by

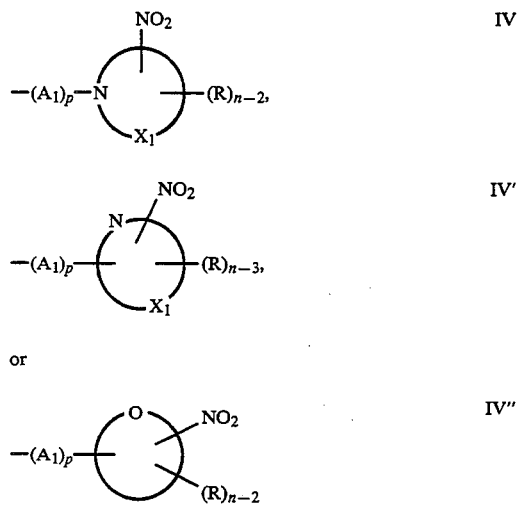

or the ring portion being a 5- or 6-membered cyclic or aromatic ring, wherein n is the total number of substitution positions available on the 5- or 6-membered ring;

the one or more R substituents are independently selected from hydrogen, halogen, alkyl, aryl, alkoxy, oxa-alkyl, hydroxyalkoxy, alkenyl, arylalkyl, arylalkylamide, alkylamide, alkylamine and (alkylamine)alkyl;

$X_1$ can be nitrogen, oxygen, sulfur, $-CR=$ or $-CRR-$; and $(A_1)_p$ can be absent in which case the $R_3$ group of formula IV, IV' or IV" is linked to the rest of the complex of this invention via a nitrogen or carbon atom, or $(A_1)_p$ is the linking group and $(A_1)_p$ can be as defined above.

The references, above, regarding hypoxia-mediated nitro-heterocyclic groups serve to illustrate that the present thinking in the art is that the reduction potential of the nitro-heterocyclic group directly affects its retention in hypoxic tissue. The spacer group, $(A_1)_p$, may therefore (in the case where $R_3$ is a hypoxia-mediated nitro-heterocyclic group) be selected not only according to its capacity to distance $R_3$ from the rest of the complex, but also in accordance with its effect on the reduction potential of the hypoxia-mediated nitro-heterocyclic group. Similarly, the present knowledge in this art provides that one skilled in the art would understand to select the values and/or positions for $A_1$, R, $X_1$ and $-NO_2$ in the groups of formula IV, IV' and IV" according to their known effects on the reduction potential as pointed out in the literature.

Preferred hypoxia-mediated nitro-heterocyclic groups are 2-, 4- and 5-nitroimidazoles which can be represented by

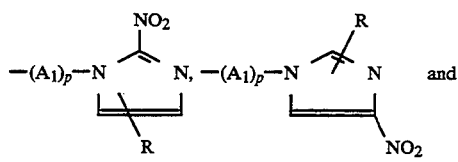

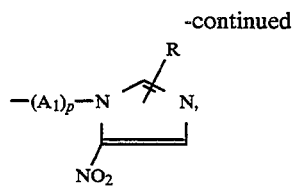

and nitrofuran and nitrothiazole derivatives, such as

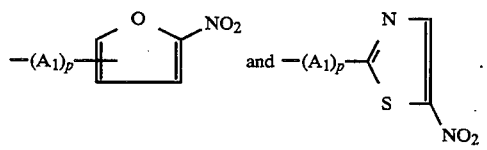

Exemplary groups (including $(A_1)_p$ spacers) include, but are not limited to,

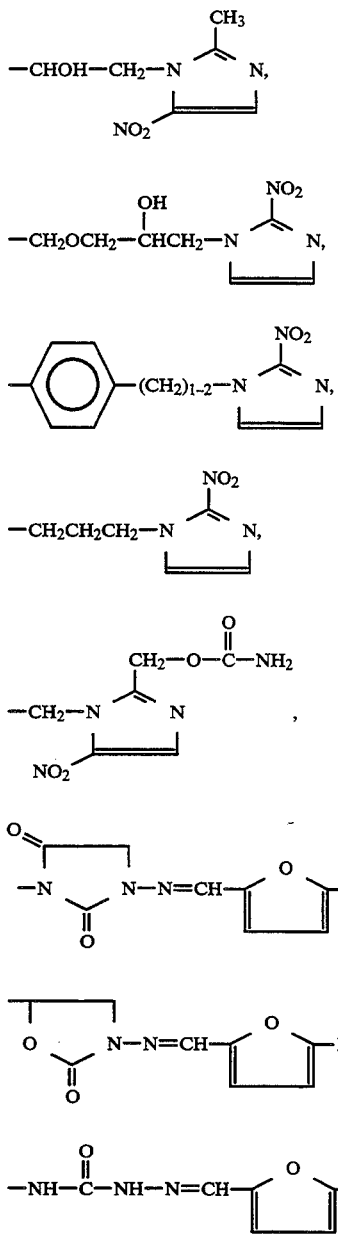

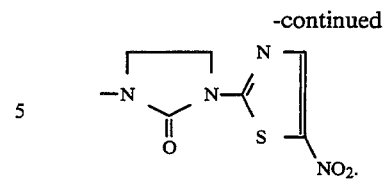

Most preferred when $R_3$ is a hypoxia-mediated nitroheterocyclic group are 2-nitroimidazoles and derivatives thereof.

When the biochemically active group at $R_3$ is asteroid it is understood that either a steroid, a substituted steroid derivative or a non-steroidal derivative can be employed provided that the $R_3$ group chosen has an affinity for the steroid receptor. For example, when $R_3$ is estradiol

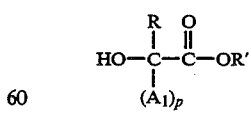

the $(A_1)_p$ linking group, or the boron atom in the case where p=0, can be at any available position on the molecule but preferably $A_1$ is linked either to an atom in the B ring or to an atom in the D ring. Additionally, the estradiol molecule may be substituted at available positions by one or more of R, wherein R is as defined above. Alternatively, 5 the steroid molecule can be replaced by a non-steroidal diol with a known affinity for the estrogen receptor, such as wherein $(A_1)_p$ and R are as defined above.

When the biochemically active group is a substrate for a muscarinic receptor, the spacer-$R_3$ portion of the complex can be represented by several possible formulae. In one of these formulae, the spacer —$R_3$ group can be represented by wherein $(A_1)_p$ and R are as defined above and R' is a tertiary or quaternary amine, such as 3-quinuclidinol or substituted 3-quinuclidinol.

Other specific compounds outside of this general structure shown are known to bind to muscarinic receptors include, but not limited to,

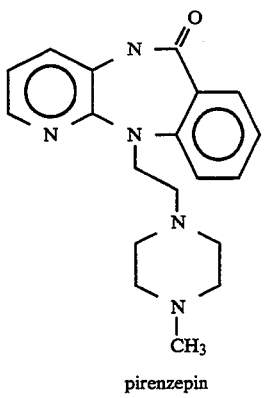

pirenzepin

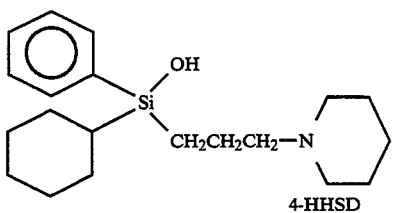

4-HHSD

All of the examples and the following process description in the case where M is rhenium involve the use of "carrier rhenium" except as otherwise noted. The phrase "carrier rhenium" means that the rhenium compounds used contain non-radioactive rhenium at concentrations of $10^{-7}$M to $10^{-5}$M.

Preparation of the complexes of this invention wherein M is rhenium can be accomplished using rhenium in the +3, +4, +5 or +7 oxidation state. Examples of compounds in which rhenium is available in the +3 oxidation state are $ReCl_3(CH_3CN)(PPh_3)_2$ and $[Re_2Cl_8](NBu_4)_2$ wherein Ph=phenyl and Bu=butyl. Re(IV) is available as $K_2ReCl_6$ and Re(VII) is available as $NH_4ReO_4$ or $KReO_4$. Re(V) is available as $[ReOCl_4](NBu_4)$ and $[ReOCl_4](AsPh_4)$ and as $ReOCl_3(PPh_3)_2$ and as $ReO_2(pyridine)_4^{\oplus}$. Other Re(III), Re(IV), Re(V), Re(VII) reagents known to those skilled in the art can also be used.

Preferably, the Re complexes of this invention are prepared using Re intermediate complexes of the formula $$ReX(Y)_3 \qquad V$$

(wherein X and Y are as defined above) which have been described in a copending application U.S. Ser. No. 398,879 filed on Aug. 28, 1989 and entitled "RHENIUM TRIS DIOXIME COMPLEX". By reacting intermediates of formula V with a boronic acid derivative of the formula

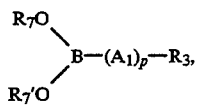

the rhenium complexes of the present invention are provided. Intermediates of formula V can be prepared using Re(III), Re(IV), Re(V) or Re(VII) reagents as described above, combined with a source of anion moiety (X), and a vicinal dioxime of formula II. This mixture should be reacted/heated at about 25° C. to 100° C for about 5 minutes to 8 hours. If Re(IV), Re(V) or Re(VII) are used, known methodologies for adding a reducing agent sufficient to reduce these starting materials to Re(III) should be employed.

Preparation of the complexes of this invention wherein M is technetium-99m can best be accomplished using technetium-99m in the form of the pertechnetate ion. The pertechnetate ion can be obtained from commercially available technetium-99m parent-daughter generators; such technetium is in the +7 oxidation state. The generation of the pertechnetate ion using this type of generator is well known in the art, and is described in more detail in U.S. Pat. Nos. 3,369,121 and 3,920,995. These generators are usually eluted with saline solution and the pertechnetate ion is obtained as the sodium salt.

This method of preparing $^{99m}Tc$ complexes, which is an alternative method to the preparation of Re complexes of this invention, includes the combining of the Re(III), Re(IV), Re(V), Re(VII) or pertechnetate ion (in the form of a salt) with a source of anion, a boronic acid derivative having formula VI or a pharmaceutically acceptable salt thereof, (wherein $R_7$ and $R_7'$ are each independently hydrogen, alkyl or aryl, or where $R_7$ and $R_7'$ taken together are $-(CR_8R_9)_n-$ wherein n is 2–6) and a dioxime having the formula

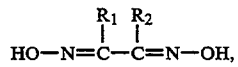

or a pharmaceutically acceptable salt thereof.

Compounds of formula VI wherein $R_3$ is a hypoxia-mediated nitro-heterocyclic group as defined in formula IV, IV' or IV'', that is,

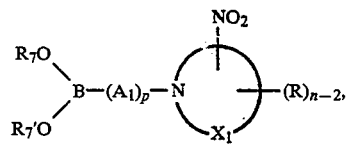

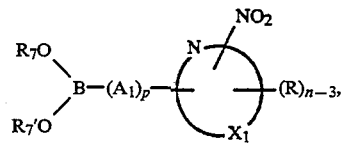

or

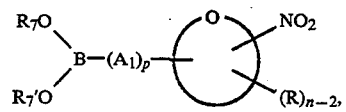

are novel intermediates and are considered a part of the present invention. These can be prepared using known methodology. For example, a boronic acid derivative of the formula

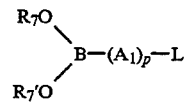

where L is a leaving group, e.g., halogen, etc., can be coupled with a compound of the formula

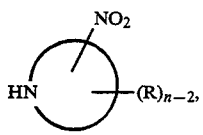

IX

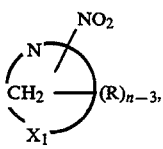

IX' or

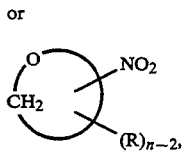

IX"

in a solvent, e.g., dimethylforamimide and in the presence of a base, e.g., potassium carbonate.

This is the preferred method for preparing the novel intermediates of formula VII. Preferably, the novel intermediates of formula VII' and VII" can be prepared by coupling a compound of the formula

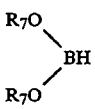

VII' or

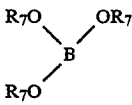

VIII"

with a compound of the formula

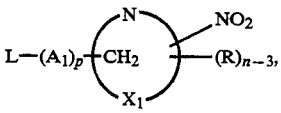

X' or

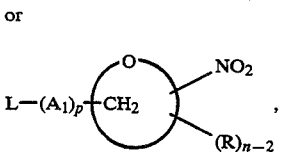

X"

in a solvent and in the presence of a base.

The source of the anion moiety (X) can be water or it can be an acid or salt which dissociates to release an appropriate anion. Exemplary anionic moieties are hydroxyl, halide, isothiocyanato (N=C=S⊖) and thiocyanato (S—C=N⊖). The preferred anionic moieties are the halides, and chloride is the most preferred halide. If the source of the anion is not water, the source should be present in an appropriate concentration to compete effectively with any water that may be present during the reaction. It has been found that the source of anion should be present in the reaction mixture in a concentration of about 0.1 to about 2.0 molar.

The boronic acid derivative of formula VI, VII, VII' or VII" should preferably be present in a concentration of about 5 to 400 millimolar. The dioxime of formula II should preferably be present in a concentration of about 9 to 250 millimolar.

The formation of the $^{99m}Tc$ complexes proceeds best if the mixture of pertechnetate ion, source of anion, boronic acid derivative, and dioxime is heated at about 25° C. to 100° C. for about 5 minutes to about 3 hours. The reaction is preferably run in an aqueous medium or aqueous alcohol mixture at a pH of less than, or equal to, about 5. Re complexes starting with Re(III), Re(IV), Re(V) or Re(VII) can also be formed using this methodology. However, as mentioned previously, for Re complexes, and also for Tc-99m complexes wherein the $R_3$ or $(A_1)_p$ group may be sensitive to the above-described temperature and pH parameters, it is preferable to react an intermediate complex $MX(Y)_3$ with a boronic acid derivative of formula VI, VII, VII' or VII". This can be done in an aqueous medium or aqueous alcohol mixture at about 25°–100° C. for about 5 minutes to 8 hours at a pH ≦5.

If pertechnetate or Re(IV), Re(V) or Re(VII) containing compounds are employed, then the reaction mixture should also contain a reducing agent. Stannous ion is the preferred reducing agent, and can be introduced in the form of a stannous salt such as a stannous halide (e.g., stannous chloride or stannous fluoride). The reducing agent should be present in a concentration of about 10 millimolar to 150 millimolar.

When the complexes of this invention are prepared, various complexing agents (also known in the art as chelating agents) can be included as part of the complexing reaction. The complexing agent should, of course, be pharmaceutically acceptable. Exemplary complexing agents are diethylenetriamine-pentaacetic acid (DTPA), ethylene glycol-bis(D-aminoethyl ether)-N,N'-tetraacetic acid (EGTA), ethylenediamine tetraacetic acid (EDTA), citric acid, tartaric acid, malonic acid, etc.

The complexing reaction mixture can also include an accelerator (catalyst) which serves to improve the radiochemical purity (i.e., percent of the radioactivity that is in the desired chemical form) of the product. Exemplary accelerators are the α-hydroxycarboxylic acids such as citric acid, tartaric acid, and malonic acid.

Working with technetium-99 or rhenium, the structure of the complexes of this invention has been investigated and is believed to be:

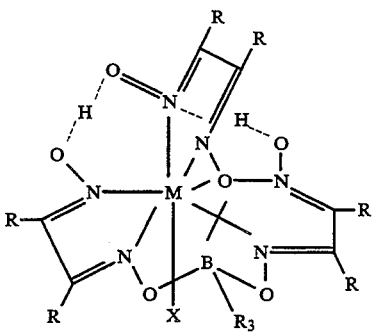

wherein M=Tc or Re.

It is convenient to prepare the complexes of this invention at, or near, the site where they are to be used. A kit having all of the components, other than the Rhenium or Technetium ion, needed to prepare the boronic adducts of Rhenium or Technetium dioxime complexes of formula I is an integral part of this invention. Such a kit contains a source of anion, a boronic acid derivative of formula VI, VII, VII' or VII", or a pharmaceutically acceptable salt thereof, a dioxime of formula II, or a pharmaceutically acceptable salt thereof, and a reducing agent. It may optionally contain a complexing agent.

The kits of this invention where M is technetium can be formulated in aqueous solution. The compounds of this invention are prepared from kits by adding pertechnetate or perrhenate in aqueous solution and heating at about 100° C. for about 10 to about 30 minutes. To optimize the stability of the kit, and to optimize the radio-chemical purity of the labeled product, the pH of the kit should be adjusted to fall within the range of about 2.0 to 5.5 using a pharmaceutically acceptable acid or base (e.g., hydrochloric acid or sodium hydroxide). Preferably, the pH of the kit will be about 3.0. It is also preferred that the kit be in lyophilized form. While kits containing some or all components in solution can be used, they are not as efficacious as the corresponding lyophilized kit. If it is necessary to isolate the desired complex, separation methods well known in the art are used.

The complexes of this invention can be administered to a host by bolus intravenous injection. The amount injected will be determined by the desired uses, e.g. to produce a useful diagnostic image or a desired radio-therapeutic effect, as is known in the art.

Preferred complexes of this invention are those wherein $R_3$ is a hypoxia-mediated nitro-heterocyclic group, an amphetamine, asteroid, or a substrate for the muscarinic receptor. Most preferred are those wherein $R_3$ is 2-nitroimidazole or a derivative thereof, [4-[2-[(1-methylethyl)amino]propylphenyl], estradiol or a derivative thereof, or 3-quinuclidinyl benzilate.

In the complexes of the present invention the preferred values for $(A_1)_p$ are alkyl, oxa-alkyl, hydroxyalkyl, hydroxyalkoxy, alkenyl, arylalkyl, arylalkylamide, alkylamide, alkylamine and (alkylamine)alkyl.

The most preferred values for $(A_1)_p$ are selected from —$(CH_2)_{2-3}$—,  —$CH_2$—CH=CH—$CH_2$—, —CH=CH—$CH_2$—,

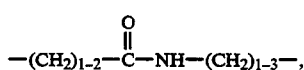

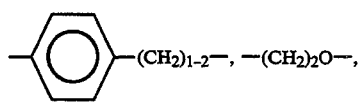

—$CH_2CH(OH)CH_2OCH_2$—,

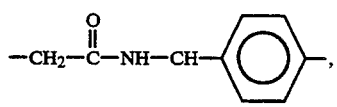

—$(A_3$—O—$A_3')_{1-3}$ and —$(A_3$—NH—$A_3')_{1-3}$; wherein $A_3$ and $A_3'$ are the same or different alkyl.

The following examples are specific embodiments of this invention.

EXAMPLE 1

[$^{99}$Tc(chloride)(dimethylglyoxime)$_3$[4-[2-[(1-methylethyl)amino]propyl]phenyl]boron]PF$_6$ 0.20429 g (1.76 mmol) of dimethylglyoxime and 0.13508 g (0.6 mmol) of [4-[2-[(1-methylethyl)amino]propyl]phenyl]boronic acid were dissolved in 20 mL of ethanol and 5 mL of water. 0.09035 g (0.5 mmol) of ammonium pertechnetate dissolved in 6 mL of 3 M HCl was added. While stirring, 0.21492 g (1.1 mmol) of stannous chloride dissolved in 5 mL of 4 M HCl was added dropwise over 5 minutes. The solution became an intense orange-brown in color. 20 mL of water were added and the reaction mixture was stirred at reflux for 2 hours. The reaction mixture was exhaustively extracted with dichloromethane, the combined $CH_2Cl_2$ fractions were dried through anhydrous sodium sulfate, and concentrated by rotoevaporation. Methanol, 4 M HCl and $NH_4PF_6$ in methanol were added to the $CH_2Cl_2$ concentrate. The desired product, as the $PF_6$—salt, precipitated on evaporation. The orange precipitate was collected by filtration, washed with water and vacuum dried. Yield: 0.122 g (31%).

Elemental analyses calc'd for TcClC$_{24}$H$_{39}$N$_7$O$_6$BPF$_6$ ½CH$_2$Cl$_2$:

C, 34.43; H, 4.68; N, 11.48; Found: C, 34.25; H, 4.45; N, 11.66.

EXAMPLE 2

$^{99m}$Tc(chloride)(dimethylglyoxime)$_3$[4-[2-[(1-methylethyl)amino]propyl]phenyl]boron Into a 5 mL siliconized serum vial were measured 1.7 mg of dimethylglyoxime, 7.0 mg of [4-[2-[(1-methylethyl)amino]propyl]phenyl]boronic acid, 20 mg of citric acid, 2 mg of DTPA, 100 mg of NaCl, and 50 μg of SnCl$_2$ (in 4 M HCl) in a total volume of 0.5 mL of saline. 0.5 mL of $^{99m}$TcO$_4$— generator eluent was added and the mixture was heated at 100° C. for 15 minutes yielding 76% of the desired product as determined by high performance liquid chromatography (HPLC). The product was purified chromatographically to give the product with 91% radiochemical purity.

EXAMPLE 3

Biodistribution Results for Amine-substituted Boron complexes, $^{99m}$Tc(chloride)(dimethylglyoxime)$_3$B-R (wherein R is or contains an amine)

Since it is well known that lipophilic amines demonstrate high lung uptake through specific binding, the lung uptake of a series of (BATO) complexes containing amine substituents in the boronic acid "cap", including the complex described in Example 2, were determined in rats. The other complexes listed were prepared using the methodology described in Example 2. Lung uptake at 5 and 60 minutes post I.V. administration of these compounds was noted. Table 1 below shows the lung uptake of the amine-containing complexes.

TABLE 1

Lung Uptake of Amine-Containing $^{99m}$Tc Comlexes
% Injected Dose in Lungs at 5 min. and 60 min. Post-injection

| Dioxime | Amine | % in Lungs 5 min. P.I. | 60 min. P.I. |
|---|---|---|---|
| DMG[1] | 4-[2-[(1-methylethyl)amino]propyl]phenyl boronic acid | 3.25 | 2.19 |
| DMG[1] | (N,N-Dimethyl-p-aminomethyl)phenylboronic acid | 1.05 | 0.52 |

TABLE 1-continued

Lung Uptake of Amine-Containing $^{99m}$Tc Comlexes
% Injected Dose in Lungs at 5 min. and 60 min. Post-injection

| Dioxime | Amine | % in Lungs 5 min. P.I. | 60 min. P.I. |
|---|---|---|---|
| DMG[1] | (N-Methyl-N-phenethyl-p-aminomethyl)phenylboronic acid | 10.59 | 4.02 |
| DMG[1] | (N-Isopropyl-p-aminophenyl) phenylboronic acid | 1.49 | — |
| DMG[1] | (N,N-Di-isopropyl-p-aminomethyl)phenylboronic acid | 0.98 | 0.46 |
| DMG[1] | p-(N,N-Diisopropyl-1-aminoethyl)phenylboronic acid | 3.37 | 1.71 |
| CDO[2] | (N,N-Dimethyl-p-aminomethyl)phenylboronic acid | 1.15 | 0.63 |
| CDO[2] | (N-Methyl-N-phenethyl-p-aminomethyl)phenylboronic acid | 4.76 | 2.77 |
| CDO[2] | (N-Isopropyl-p-aminophenyl) phenylboronic acid | 3.07 | 1.37 |
| CDO[2] | (N,N-Di-isopropyl-p-aminomethyl)phenylboronic acid | 5.89 | 3.50 |
| CDO[2] | p-(N,N-Diisopropyl-1-aminoethyl)phenylboronic acid | 3.12 | 1.58 |
| CDO[2] | N-Ethyl-N-isopropyl-p-aminomethylphenylboronic acid | 5.59 | 3.89 |

[1]DMG = Dimethylglyoxime
[2]CDO = 1,2-Cyclohexanedione dioxime

EXAMPLE 4

$^{99}$Tc(chloride)(dimethylglyoxime)$_3$(estradiol boron)

0.02796 g (0.058 mmol) of $^{99}$Tc(chloride)dimethylglyoxime)$_3$ was dissolved in 10 mL of acetonitrile. While stirring, 0.02449 g (0.072 mmol) of estradiol boronic acid, [17α(E)-3,17-dihydroxy-1,3,5(10)-estratrien-17-yl]ethenylboronic acid, was added as a solid. 2 mL of 1 M HCl were added and the reaction mixture was stirred with gentle heating for 1 to 2 hours. Addition of 1 M HCl (3 to 5 mL) resulted in the precipitation of the product. The product was recrystallized from acetonitrile/1 M HCl. Yield: 0.022 g (48%).

Elemental analyses calc'd for: TcClC$_{32}$H$_{45}$N$_6$O$_8$B $\frac{1}{2}$ H$_2$O: C, 48.27; H, 5.78; N, 10.56;
Found: C, 48.26; H, 5.70; N, 10.50.

EXAMPLE 5

$^{99m}$Tc(chloride)dimethylglyoxime)$_3$(estradiol boron)

Into a 5 mL siliconized serum vial were measured 2.0 mg of dimethylglyoxime, 2.2 mg of estradiol boronic acid, 20 mg of citric acid, 100 mg of NaCl and 100 ug of SnCl$_2$ (in 4 M HCl) in a total volume of 0.6 mL of 33% ethanol/saline. 0.5 mL of $^{99m}$TcO$_4^-$ generator eluent was added and the mixture was heated at 100° C. for 15 minutes, yielding 70% of the desired compound as determined by HPLC.

EXAMPLE 6

$^{99m/99}$Tc(chloride)(dimethylglyoxime)$_3$(estradiol boron) of known specific activity for in vitro estrogen receptor binding studies Samples were prepared containing both $^{99}$Tc and $^{99m}$Tc in order to determine the specific activity (Ci/mmol) accurately. Samples were prepared in the following manner: 2 mg of estradiol boronic acid, 0.2 mL of dimethylglyoxime (10 mg/mL of ethanol), 0.2 mL of citric acid (100 mg/mL of H$_2$O), 0.2 mL of saturated NaCl (in H$_2$O), 0.100 mL of NH$_4$$^{99}$TCO$_4$ (3.66×10$^{-4}$ M in H$_2$O) and 0.1 mL to 0.5 mL of $^{99m}$TcO$_4^-$(eluent from a Mo99/Tc99m generator), to give the desired specific activity, were combined in a 5 mL siliconized vial. 10 μL of SnCl$_2$ (0.100 g dissolved in 1 mL of conc. HCl and diluted to 4 mL with H$_2$O) were added to the reaction vial. The sample was heated for 15 minutes at 100° C., cooled for 5 minutes and purified chromatographically (PRP-1 resin) to yield the product in >95% purity.

EXAMPLE 7

In vitro estrogen receptor binding studies using $^{99m/99}$Tc( chloride) dimethylglyoxime)$_3$(estradiol boron)

The methods used for the receptor binding studies have been previously described by E. M. Jagoda et al., J. Nucl. Med. 1984, 25 472–7. "[$^{125}$I]-17-Iodovinyl-11-Methoxyestradiol: In Vivo and In Vitro Properties of a High Affinity Estrogen-Receptor Radiopharmaceutical". Receptor binding studies using cytosolic preparations of isolated rat uteri from 20–25 day old female rats were performed to determine the affinity of the technetium labeled estradiol for the estrogen receptor. Preparations of the compound ranged in specific activity from 400 to 2000 Ci/mmol and the specific binding ranged from 10–30% of the total bound activity.

EXAMPLE 8

$^{99m/99}$TcCl(dimethylglyoxime)$_3$(QNB-boron) of known specific activity for in vitro muscarinic receptor binding studies Samples were prepared containing both $^{99}$Tc and $^{99m}$Tc in order to determine the specific activity (Ci/mmol) accurately. Samples were prepared in the following manner: 2 mg of 3-Quinuclidinyl-(4-boronobenzilate) (QNB-boronic acid prepared as described by G. W. Kabalka et al., Nucl. Med. Biolo 1989, 16(4), 359–360), 0.2 mL of dimethylglyoxime (10 mg/mL of ethanol), 0.2 mL of citric acid (100 mg/mL of H$_2$O), 0.2 mL of saturated NaCl (in H$_2$O), 0.1 mL of DTPA (20 mg/mL of 0.5 M NaOH), 0.2 mL of gamma-cyclodextrin (25% w/v H$_2$O), 0.100 mL of NH$_4$$^{99}$TcO$_4$ (3.66×10$^{-4}$ M in H$_2$O) and 0.1 to 0.5 mL of $^{99m}$TcO$_4^-$ (eluent from a Mo99/Tc99m generator), to give the desired specific activity, were combined in a 5 mL siliconized vial. 10 μL of SnCl$_2$ (0.100 g dissolved in 1 mL of concentrated HCl and diluted to 4 mL with H$_2$O) were added to the reaction vial. The sample was heated for 15 minutes at 100° C., cooled for 5 minutes and purified chromatographically (PRP-1 resin) to yield the product in 90–95% purity.

EXAMPLE 9

In vitro muscarinic receptor binding studies using $^{99m/99}$Tc(chloride)(dimethylglyoxime)$_3$(QNB boron)

The methods used for the receptor binding studies have been previously described by R. E. Gibson, W. J. Rzeszotarski, W. C. Eckelman, E. M. Jagoda, D. J. Weckstein, R. C. Reba, Biochemical Pharmacology, 1983, 32(12), 1851–1856. Receptor binding studies using rat caudate putamen isolated from rat brain were performed to determine the affinity of the technetium labeled QNB for the muscarinic receptor. Preparations of the compound ranged in specific activity from 600–1000 Ci/mmol and the specific binding ranged from 5–20% of the total bound activity.

EXAMPLE 10

Preparation of 1-(2-Nitroimidazole)-benzylboronic acid

A. Preparation of p-tolylboronic acid p-Bromotoluene (17.1 g, 0.1 mole) in 150 mL of ether was added dropwise into a mixture of magnesium (2.5 g, 0.105 mole) in 30 mL of ether in a 200 ml reaction vessel. The reaction mixture was stirred overnight at room temperature. The dark brown solution was transferred into an addition funnel via a transfer needle, by nitrogen gas pressure.

This Grignard reagent was added dropwise over a period of 1.5 hours into a solution of trimethylborate (10.4 g, 0.1 mole) in 200 mL of ether at −78° C. under nitrogen gas. After stirring overnight at ambient temperature, the resultant off-white reaction mixture was hydrolyzed with 200 mL of water and acidified with 35 mL of 3N sulfuric acid. The aqueous layer was extracted with ether (4×80 mL). The combined organic layer was washed and dried over sodium sulfate. Removal of solvent afforded a white solid which was recrystallized from water. Yield 6.1 g (45%), m.p. 251°–256° C. (Lit. 259° C.) $^1$HNMR (DMSO) $\delta$2.25 (s, 3H,—CH$_3$); 7.12 and 7.64 (d, 4H, ArH); 7.86 (s, 2H,—BOH).

B. p-bromomethylbenzene boronic acid 5 mL of bromine solution (2.4 g, 1.5×10$^{-2}$ mole) in 20 mL of carbon tetrachloride was added to a solution of p-tolylboronic acid (2.0 g, 1.47×10$^{-2}$ mole) in 40 mL of carbon tetrachloride. The reaction was initiated by illumination with a 150 Watt light bulb. The bromine color faded in 5 minutes and the remaining bromine solution was added over 15 minutes. A solid product precipitated during bromine addition. The solid was filtered and crystallized from chloroform. Yield 1.5 g (49%), m.p. 154°–156° C., $^1$HNMR (DMSO) $\delta$4.18(s,2H,—CH$_2$Br); 7.37 and 7.74(d,4H,—ArH).

C. Preparation of 1-(2-Nitroimidazoyl)benzylboronic acid

2-Nitroimidazole (100 mg, 8.85×10$^{-4}$ mole, previously purified by sublimation) and p-bromomethylbenzeneboronic acid (190 mg, 8.85×10$^{-4}$ mole) were mixed with 20 mg of potassium carbonate in 30 mL of dry acetone in a 50 mL one neck round bottom flask equipped with a reflux condenser. The reaction mixture was stirred and heated under reflux, under nitrogen gas, for 16 hours. The light green-yellow solution was filtered and the filtrate evaporated to dryness under reduced pressure to afford a light yellow solid. The product was recrystallized from water. Yield 150 mg (69%). m.p. 212°–214° C., $^1$HNMR (DMSO) $\delta$5.6 (s, 2H, CH$_2$Ar), 7.1 and 7.75 (d,4H,ArH); 7.25 and 7.75 (s,2H, CH=CH).

EXAMPLE 11

Preparation of 4-(2-Nitroimidazolyl ethyl)phenyl boronic acid

A. Preparation of 2-(4-bromophenyl)-1-O-t butyldimethyl silyl ethane

4-Bromophenyl ethyl alcohol (4.0 g, 20 mmol) and imidazole (3.4 g, 50 mmol) were dissolved in dry dichloromethane (100 ml), treated with t-butyl dimethyl silyl-chloride (3.1 g, 20 mmol) and stirred for 6 hours under nitrogen at room temperature. The resultant product was washed with water, dried, concentrated and distilled under vacuum. Yield 6.0 g (95%), b.p. 115°–117° C./0.7 mm, M.S. 314 and 316(m/e) $^1$H NMR (CDCl$_3$), $\delta$0.05 (s, 6H), 0.9 (s, 9H), 2.8 (t, 2H), 3.85 (t, 2H) and 7.5 (AB q, 4H).

B. Preparation of 4-(2-hydroxy ethyl)phenyl boronic acid

To a suspension of magnesium (0.264 g, 11 mmol) in dry tetrahydrofuran (10 ml) under nitrogen gas was added dropwise over $\frac{1}{2}$ hour the t-butyl dimethyl silyl ether of 4-bromophenyl ethyl alcohol (a, 3.45 g, 10.9 mmol) in tetrahydrofuran (10 ml). Magnesium was then activated by the addition of dibromoethane (0.1 g). The metal went into solution slowly over a period of 8 hours. The Grignard reagent was then cooled to −78° C. and treated with freshly distilled trimethyl borate (1.15 g, 11 mmol) added dropwise with stirring. The reaction mixture was then warmed to room temperature and stirred overnight. It was then treated with 2N hydrochloric acid till acidic and the tetrahydrofuran layer was separated from the aqueous layer. The aqueous portion was thoroughly extracted with ethyl acetate (5×50 ml) and the combined organic layer was washed with water and finally with saturated sodium chloride. The organic phase was then dried, concentrated and the residue was purified by chromatography (silica gel). Elution with ethyl acetate/methanol (95:5) provided the boronic acid, which was recrystallized from ethyl acetate/hexane. Yield: 0.69 g (38%), m.p. 218°–220° C., M.S. 184 (M+NH$_4$), 156, 140, $^1$H NMR (DMSO-d$_6$): $\delta$2.7 (t, 2H), 4.6 (t, 2H), 7.1 and 7.7 (2d, 4H) and 7.9 (s, 2H).

C. Preparation of 4-(2-bromoethyl)phenyl boronic acid

To a solution of 4-(2-hydroxyethyl)phenyl boronic acid (1.66 g, 10 mmol) in dry dimethylformamide (25 ml), was added ethylene glycol (0.62 g, 10 mmol). The mixture was stirred under nitrogen at room temperature for 16 hours. Dimethylformamide was removed under reduced pressure and the resulting oil was kept under vacuum for 6 hours more. The oil was dissolved again in dry dimethylformamide (10 ml), cooled in an ice-bath, treated with triphenyl phosphine (5.25 g, 20 mmol) and N-bromosuccinimide (3.56 g, 20 mmol), and stirred under nitrogen for 6 hours at room temperature. Solvent was removed under reduced pressure and the residue was taken up in ether (100 ml). This was washed with water, dried and concentrated to give an oil which was chromatographed to furnish the bromo boronic acid as a colorless solid (silica gel, 1:1 ethyl acetate/hexane). The product was recrystallized from dichloromethane/hexane. Yield: 1.4 g, m.p. 146°–148° C.

D. Preparation of 4-(2-Nitroimidazolyl ethyl)phenyl boronic acid 4-(2-Bromoethyl)phenyl boronic acid (0.525 g, 2.72 mmol) and 2-nitroimidazole (0.3 g, 2.72 mmol) were heated in dry dimethylformamide (15 ml) in presence of anhydrous potassium carbonate (1.38 g, 10 mmol) under nitrogen with stirring at 60°–70° C. for 48 hours. Dimethylformamide was removed under reduced pressure and the resulting gum was dissolved in a minimum amount of water and acidified with 2N hydrochloric acid. The precipitated solid was filtered off and washed with water. The combined aqueous portion was again extracted with ethyl acetate (5×50 ml). The organic layer was dried, concentrated and combined with the previously precipitated solid and chromatographed (silica gel). Elution with 1:1 ethyl acetate/hexane yielded some unreacted starting bromide (0.1 g); continued elution with 2:1 ethyl acetate/hexane provided the required boronic acid as a pale yellow crystalline solid. The product was recrystallized from tetrahydrofuran/hexane. Yield: 0.25 g (36%), m.p. 229°–231° C., M.S. (M+H)+262.

$^1$H NMR (DMSO-d$_6$): δ3.1 (t, 2H), 4.65 (t, 2H), 7.11 (d, 2H), 7.14 (s, 1H), 7.5 (s, 1H), 7.69 (d, 2H) and 7.94 (s, 2H).

EXAMPLE 12

Preparation of $^{99m}$Tc(chlorine)(1,2-cyclohexanedionedioxime)$_3$1-(2-nitroimidazoyl)benzylboron To a mixture of 10 mg citric acid, 100 mg of sodium chloride, 2 mg of 1,2-cyclohexanedione dioxime, 2 mg of diethylenetriamine-penta-acetic acid, 50 mg of gammacyclodextrin, 50 μg of stannous chloride, and 3 mg of 1-(2-nitroimidazoyl)benzyl boronic acid was added 1 mL of sodium pertechnetate ($^{99m}$TcO$_4$−) in physiological saline. The kit was heated at 100° C. for 15 minutes. The yield of the title compound, as determined by HPLC, was 91.4%. Samples of this complex coeluted from Nucleosil C-8 reverse phase HPLC columns at a retention time identical to that of an authentic $^{99}$Tc standard that was prepared as described below.

EXAMPLE 13

Preparation of $^{99}$Tc(chlorine)(1,2-cyclohexanedione dioxime)$_3$1-(2-nitroimidazoyl)benzyl boron To 90.3 mg (0.11 mmol) of $^{99}$Tc(1,2-cyclohexanedione dioxime)$_3$(μ-OH)SnCl$_3$ dissolved in 10 mL of warm acetonitrile was added 1-(2-nitroimidazoyl)benzylboronic acid (31 mg, 0.125 mmol) and 1.5 mL of 3N hydrochloric acid. The solution was heated gently, with stirring. After 30 minutes, 10 mL of 1M hydrochloric acid was added, and the 0 solution was cooled to room temperature. The resulting orange precipitate (61 mg, 78% yield) was recrystallized from warm acetonitrile/1M hydrochloric acid.

Analysis calc'd for C$_{28}$H$_{34}$N$_9$BClO$_8$Tc: C, 43.59; H, 4.43; N, 16.20; Found: C, 43.68; H, 4.45; N, 16.37.

A strong protonated molecular ion (M+H)+was observed at m/z=770. Samples of this complex eluted from nucleosil C-8 reverse phase HPLC columns with a retention time of 2.34 minutes (80/20 ACN/0.1 M citric acid, 1.5 mL/minute).

EXAMPLE 14

Preparation of $^{99m}$Tc(chlorine)(dimethylglyoxime)$_3$-1-(2-nitroimidazoyl)benzylboron To a freeze-dried mixture of 2 mg of dimethylglyoxime, 18 mg citric acid, 100 mg of sodium chloride, 1 mg of diethylenetriamine-pentaacetic acid, 50 mg of gammacyclodextrin, 50 μg of stannous chloride, and 3 mg of 1-(2-nitroimidazoyl)benzyl boronic acid was added 1 mL of sodium pertechnetate ($^{99m}$TcO$_4$−) in physiological saline. The kit was heated at 100° C. for 15 minutes. The yield of the title compound, as determined by HPLC, was 73.4%. Samples of this complex eluted from Nucleosil C-8 reverse phase HPLC columns at a retention time identical to that of an authentic $^{99}$Tc standard that was prepared as described below.

EXAMPLE 15

Preparation of $^{99}$Tc(chlorine)(dimethylglyoxime)$_3$-1-(2-nitroimidazoyl)benzylboron To 55 mg of $^{99}$Tc(dimethylglyoxime)$_3$(μ-OH)-SnCl$_3$ (0.074 mmol) was added 25 mg (0.10 mmol) of 1-(2-nitroimidazoyl)benzylboronic acid, dissolved in 10 mL of acetonitrile. One mL of 3N hydrochloric acid was added, and the solution was heated gently 0 for 30 minutes. Ten mL of 1M hydrochloric acid was added, and the solution was cooled to room temperature. The resultant orange crystals (32 mg, 62.3% yield) were recrystallized from a warm acetonitrile/1M hydrochloric acid solution to give analytically pure complex, isolated as the 0.5 H$_2$O hydrate.

Analysis calc'd for C$_{22}$H$_{29}$N$_9$BClO$_{8.5}$Tc: C, 37.62; H, 4.33; N, 17.63; Found: C, 37.71; H, 4.17; N, 17.99.

Samples of this complex eluted from Nucleosil C-8 reverse phase HPLC columns at a retention time of 3.45 minutes (60/40 ACN/0.1 M citric acid, 1.5 mL/minute).

EXAMPLE 16

Preparation of $^{99m}$Tc(chlorine)(dimethylglyoxime)$_3$-4-(2-nitroimidazolylethyl)phenyl Boron To a mixture of 18 mg citric acid, 100 mg of sodium chloride, 2 mg of dimethylglyoxime, 1 mg of diethylenetriamine-penta-acetic acid, 50 mg of gammacyclodextrin, 50 μg of stannous chloride and 3 mg of 4-(2-nitroimidazolyl ethyl)phenyl boronic acid was added 20 mCi of $^{99m}$TcO$_4$−in 1 ml of physiological saline. The kit was heated at 100° C. for 15 minutes to give 93% yield of the title complex, as determined by HPLC.

EXAMPLE 17

Compounds containing nitro-heterocyclic groups are retained in hypoxic tissue by reduction of the nitromoiety in such groups. Therefore, redox potential for nitro-heterocyclic groups is considered to be an indicator of the degree to which such groups can be retained by hypoxic tissue.

Cyclic voltammetry studies in DMF solvents were performed using a standard 3-electrode configuration (Heinze, J. Ang. Chem. Int., Ed. Eng., 23, 831, 1984). Data were obtained using a PAR 174A polarographic analyzer interfaced with PAR 303 static mercury drop electrode apparatus and recorded on a PAR RE0074 X-Y recorder. The reference electrode was Ag/AgNO$_3$ in acetonitrile; the working electrode was mercury.

Sample solutions, typically 0.3–1.2 mM, contained 0.1M tetrabutylammonium tetrafluoroborate supporting electrolyte, and were degassed with solvent-saturated N$_2$ before measurements.

TABLE 2

| Electrochemistry Results from DMF Peak Potential (EP) Values-(scan rate = 100 mV/sec) | | |
|---|---|---|
| | Nitro-base | |
| Compound | Cathodic | Anodic |
| Simple Nitroimidazoles | | |
| 1-(2-Nitroimidazoyl)benzyl boronic acid | −1.54 | −1.43 |

TABLE 2-continued

Electrochemistry Results from DMF
Peak Potential (EP) Values-(scan rate = 100 mV/sec)

| Compound | Nitro-base Cathodic | Anodic |
|---|---|---|
| Metronidazole | −1.63 | −1.55 |
| Misonidazole | −1.51 | −1.43 |
| Simple BATO[1] | | |
| TcCl(DMG)$_3$BMe[2] | — | — |
| BATO Nitroimidazoles | | |
| Complex of Example 15 | −1.58 | −1.51 |
| Complex of Example 13 | −1.56 | −1.50 |

[1]BATO is boronic acid technetium oxime and refers to the boronic trioxime complexes of technetium.
[2]Technetium(chloride)(dimethylglyoxime)$_3$(methyl boron).

EXAMPLE 18

Previous in vitro and in vivo studies with nitroimidazole containing compounds have demonstrated that a probable mechanism for intracellular binding of nitroimidazoles results from enzymatic reduction of the nitro group to a chemically reactive species (for example, Clarke, Wardman, and Goulding, Biochem. Pharmacol. (1980) 29, 2684–2687). The nitroimidazole boronic acids in this invention were examined in an assay using the enzyme xanthine oxidase. Assay solutions contained the following

| Hypoxanthine | 1 ml of 0.01M solution = 10 μmoles of substrate |
|---|---|
| xanthine oxidase | 0.5 Units in 500 μl of pH 7.4 Na phosphate buffer |
| Na phosphate buffer | 1.0 ml, 0.1M, pH 7.4, 10 mg/L Na$_2$EDTA |
| Nitro compound | 0.25 μMoles in 20 μl of dimethylformamide |

Reactions were initiated by adding enzyme to a solution of all other reagents in a septum-sealed cuvette. All reagents were degassed prior to mixing by passage of argon over the surface for 20 minutes. Loss of the nitro group (an indication of reduction) was monitored every 5 minutes using a UV/Visible spectrophotometer set at 326 nm. The half-lives of disappearance of the nitro compounds were determined by plotting log (concentration) mmole/ml vs time for all compounds studied. The results are shown in table 3, with data on two reference compounds, misonidazole and metronidazole shown for comparison.

TABLE 3

| COMPOUND | half life (enzyme assay) | Epc(DMF)* | Epc(Aqueous)** |
|---|---|---|---|
| Metronidazole | >24 hr | −1.62 V | −0.46 V |
| BB4NO2 | 95 min. | −1.80 V | −0.50 V |
| Misonidazole | 45 min. | −1.49 V | −0.33 V |
| BPhEtNO2 | 42.5 min. | −1.53 V | −0.30 V |
| BPropeneNO2 | 24 min. | −1.56 V | −0.30 V |
| BBNO2 | 11 min. | −1.52 V | −0.32 V |

*Electrochemical peak potential (cathodic) in DMF vs. Ag/AgNO$_3$.
**Electrochemical peak potential (cathodic) in water vs. saturated calomel electrode.

EXAMPLE 19

Preparation of 2-Nitroimidazolyl-N$_1$-[2-propenyl]-3-boronic acid (BpropenNO$_2$)

2-Nitroimidazole (1.0 g, 8.84 mmol) in dry dimethylformamide (15 ml) was treated with anhydrous potassium carbonate (6.9 g, 50 mmol) and stirred for 0.5 hr. at room temperature Under nitrogen. The solution was cooled to 0° C. and then treated with 2-bromoethyl-2-ethenyl-1,3,2-benzodioxoborole (4.23 g, 17.7 mmol) in dry tetrahydrofuran (10 ml) over a period of 1 hour with stirring under nitrogen at 0° C. The reaction mixture was then heated at 60°–70° C. for 48 hours with stirring under nitrogen, dimethylformamide was removed under reduced pressure and the residue was dissolved in methanol (100 ml). The solution was acidified with Dowex 50×8 resin (H+) and filtered. The resin was washed with methanol and the combined filtrate and wash was concentrated and chromatographed to yield a semi solid (silica gel, 230–400 mesh, 2% methanol in EtOAc) which was recrystallized from dichloromethane to give a pale yellow crystalline solid. Yield: 0.3 g, m.p. 138°–140° C.

$^1$HNMR (DMSO-d$_6$): δ5.2 (d, 2H), 6.6 (m, 1H), 7.15 (s, 1H), 7.4 (s, 1H) and 7.7 (s, 2H) Analysis: Calculated for C$_6$H$_8$BN$_3$O$_4$, C 36.59, H 4.09, N 21.34, Found C 36.79, H 3.66, N 21.41.

EXAMPLE 20

2-Nitroimidazolyl-N-propyl-3-boronic acid (BpropNO$_2$)

A mixture of hydroxylamine hydrochloride (0.417 g, 6 mmol), sodium acetate (0.492g, 6 mmol), ethylacetate (0.176 g, 2 mmol) and BpropenNO$_2$ (Example 19, 0.2 g, 1 mmol) in ethanol (25 ml) was refluxed with stirring under argon for 30 hours. After cooling, the solvent was removed, and the crude product was directly loaded on to a flash silica gel column and chromatographed. The isolated product was rechromatographed twice more to yield the product as a pale yellow solid. Yield: 0.02 to 0.025 g (20–25%) m.p. 122°–124° C. $^1$H NMR (DMSO-d$_6$): δ0.8 (t, 2H, B-CH$_2$), 1.9 (m, 2H), 4.4 (t, 2H, N-CH$_2$), 7.2 (s, 1H), 7.8 (s, 2H, B-OH) and 7.85 (s, 1H) M.S. (M+H)$^+$- 200, 172, 154 and 109. Analysis: Calculated for C$_6$H$_{10}$N$_3$BO$_4$:: C 36.22, H 5.02, N 21.11 Found: C 36.87, H 4.84, N 21.56.

EXAMPLE 21

Preparation of 1-(4-Nitroimidazole)-benzylboronic acid (BB4NO$_2$)

This compound was prepared by reaction of 4-nitroimidazole (1.13 g, 10mmol) and 4-bromomethyl-phenyl boric acid (3.25 g, 15 mmol), by the method described in Example 10. Yield: 1.7 g; m.p. 163°–165° C. $^1$H NMR [DMSO-d$_6$]: δ5.4 (s, 2H), 7.4 (d, 2H), 7.9 (d, 2H), 8.2 (bs, 2H) and 8.6 (s, 1H). $^{13}$C NMR [DMSO-d$_6$]: δ50.76, 121.59, 126.86, 134.54, 134.66, 137.45, 137.89 and 147.18. Analysis: Calculated for C$_{10}$H$_{10}$BN$_3$O$_4$ C 48.62, H 4.08 N 17.01. Found C 49.39, H 4.21, N 16.83. M.S. [M+Gly-2 H$_2$O+H]$^+$304.

EXAMPLE 22

Preparation of $^{99}$TcCl(DMG)$_3$BPhEtNO$_2$

To Tc(DMG)$_3$(μ-OH)SnCl$_3$H$_2$O (77.1 mg, 0.104 mmol) in 5 ml of acetonitrile was added BPhEtNO2

(Example 11, 28.8 mg, 0.11 mmol), followed by 2 drops of conc. HCl. The solution was heated at a boil for 30 minutes during which time an orange solid precipitated (68 mg, 93% yield). The precipitate was isolated by filtration and was washed well with acetonitrile and dried in vacuo. This solid was dissolved in 1 ml of dimethylformamide, 2 ml of acetonitrile and 1 ml of 1M hydrochloric acid and the solution was boiled for 30 minutes. Crystals of the product (31 mg, 40% overall yield) formed upon cooling overnight. Anal. Calcd for $TcCl(DMG)_3BPhEtNO_2$. 0.5DMF, $C_{24.5}H_{33}N_{9.5}BClO_{8.5}Tc$. Found: C, 39.80, H, 4.60; N, 17.55. Calcd: C, 39.64; H, 4.81; N, 17.92.

EXAMPLE 23

Preparation of
$^{99m}Tc$(chlorine)(dimethylglyoxime)$_3$-1-(n-propyl-2-nitroimidazolyl)boron The title compound was prepared as described in Example 14, except that 4 mg of BpropNO$_2$(example 20) was substituted for the 1-(2-nitroimidazolyl)-benzyl boronic acid. The yield of title complex, as determined by HPLC, was 52%. Samples of this complex eluted from a Nucleosil C-8 reverse phase HPLC column with a retention time identical to that of an authentic $^{99}Tc$ standard that was prepared as described in Example 24.

EXAMPLE 24

Preparation of $^{99}Tc$ (chlorine)(dimethyl glyoxime)$_3$-1-(n-propyl-2-nitroimidazolyl)boron To Tc(DMG)$_3$($\mu$-OH)SnCl$_3$·3H$_2$O in 10 ml of acetonitrile was added BPropNO$_2$ (example 20, 41.8 mg, 0.21 mmol), followed by 3 ml of 2N HCl. The reaction mixture was heated gently for 30 minutes, 50 ml of 1N hydrochloric acid was added, and the solution was cooled to room temperature. The resultant flocculant orange solid was isolated by suction filtration, washed with 1M hydrochloric acid and H$_2$O and dried in vacuo to yield 97 mg (78%) crude product. This was dissolved in 1 ml of CHCl$_3$ and chromatographed on a 1×10 cm silica gel column that was conditioned and eluted with CHCl$_3$. The major orange band was evaporated to dryness, redissolved in 3 ml of CH$_2$Cl$_2$ and treated with 30 ml of hexaneo Analytically pure solid was isolated in 57% yield overall. Anal. Calc for $C_{18}H_{28}N_9BClO_8Tc$. Found: C, 33.66; H, 4.20; N, 19.28. Calc: C, 33.58; H, 4.38; N, 19.58.

EXAMPLE 25

Preparation of
$^{99m}Tc$(chlorine)(dimethylglyoxime)$_3$-1-(propene-2-nitroimidazolyl)boron The title compound was prepared as described in Example 14, except that 3 mg of BpropenNO$_2$(Example 19) was substituted for the 1-(2-nitroimidazolyl)-benzyl boronic acid. The yield of title complex, as determined by HPLC, was 58%.

EXAMPLE 26

Preparation of
$^{99M}TC$(chlorine)(dimethylglyoxime)$_3$-1-(4-nitroimidazolyl)benzylboron The title compound was prepared as described in Example 14, except that 3 mg of BB4NO$_2$ (Example 21) was substituted for the 1-(2-nitroimidazolyl)benzyl boronic acid. The yield of the title complex, as determined by HPLC, was 82%. Samples of this complex eluted from a PRP-1 HPLC column with a retention time identical to that of an authentic $^{99}Tc$ standard, prepared as described in Example 27.

EXAMPLE 27

Preparation of
$^{99}Tc$(chlorine)(dimethylglyoxime)$_3$-1-(4-nitroimidazolyl)benzylboron A mixture of $^{99}TcCl(DMG)_3$(32.7 mg, 0.068 mmol) and BB4NO$_2$ (example 21, 17.7 mg, 0.073 mmol) in 5 ml of acetonitrile and 0.5 ml of 2N HCl was heated with stirring for 15 minutes. Solvents were then removed by evaporation. The product was purified on a silica gel column eluted with 40/60 ACN/CH$_2$Cl$_2$. The major orange band was evaporated to dryness and recrystallized from ether (61% yield). Anal. Calcd for $TcCl(DMG)_3BB4NO_2.0.2$ $C_4H_{10}O$ ($C_{22}H_8N_9O_8B$-$ClTc.0.2C_4H_{10}O$. Found: C, 38.39; H, 4.21; N, 17.44. Calcd: C, 38.75; H, 4.28; N, 17.84. FAB-MS(+): m/z 692, [M+H]; 656, [M-Cl]; 579, [M-4-nitroimidazole]. $^1$H NMR (270 MHz, CDCl$_3$): δ2.4 (m, 18H, Me), 5.2 (s, 2H, Bz), 7.2 (d, 2H, Ph), 7.5 (s, 1H, imidazole), 7.7 (s, 1H, imidazole), 7.8 (d, 2H, Ph), 14.8 (s, 2H, oxime). IR (KBr) (cm$^{-1}$): 3505 br, 1634, 1545, 1491, 1399, 1338, 1228, 1206 s, 1089 s, 990 s, 928, 909, 824, 808. UV-VIS (CH$_3$CN):λmax(Logε) 288(4.08), 382 (3.80), 460 (3.41).

EXAMPLE 28

Preparation of
$^{99m}Tc$(chlorine)(1,2-cyclohexane-dionedioxime)$_3$-1-(4-nitroimidazolyl)benzylboron The title compound was prepared as described in Example 12, except that 3 mg of BB4NO$_2$ (Example 21) was substituted for the 1-(2-nitroimidazolyl)benzyl boronic acid. The yield of title complex, as determined by HPLC, was 86%. Samples of this complex eluted from PRP-1 HPLC columns at a retention time identical to that of an authentic $^{99}Tc$ standard that was prepared as described below.

EXAMPLE 29

Preparation of
$^{99}Tc$(chlorine)(1,2-cyclohexane-dionedioxime)$_3$-1-(4-nitroimidazolyl)benzylboron A mixture of TcCl(CDO)$_3$ (25.7 mg, 0.046 mmol) and BB4NO$_2$ (Example 21, 11.6 mg, 0.048 mmol) was dissolved in 5 ml of ACN and 0.5 ml of 3M hydrochloric acid and heated with stirring for 30 minutes. Orange solid was precipitated by adding 5 ml of 1M hydrochloric acid and collected by filtration (crude yield, 83%).

Anal. Calcd. for $C_{28}H_{34}N_9O_8ClBTc$. 0.5 $C_4H_{10}O$: C, 44.65; H, 4.87; N, 15.62. Found: C, 44.81; H, 4.95; N, 16.05. FAB-MS(+): m/z 769, M; 734, $^1$H NMR (270 MHz, CDCl$_3$): δ2.9 (m, 12H, CDO), 3.0 (m, 12 H, CDO), 5.2 (s, 2H, Bz), 7.2 (d, 2H, Ph), 7.4 (s, 1H, imidazole), 7.7 (s, 1H, imidazole), 7.8 (d, 2H, Ph), 14.8 (s, 2H, oxime). IR (KBr) (cm$^{-1}$): 3450 br, 1631, 1546, 1446, 1430, 1380, 1337, 1286, 1229, 1203 s, 1061 s, 960 s, 924, 902, 866, 847. UV-VIS (CH$_3$CN):λmax(Logε) 290(4.35), 386(4.11), 462(3.76).

EXAMPLE 30

Preparation of $^{99m}$Tc(hydroxy)(dimethylglyoxime)$_3$-1-(2-nitroimidazolyl)benzylboron The compound $^{99m}$Tc(chlorine)(dimethylglyoxime)$_3$-1-(2-nitroimidazolyl)benzylboron was prepared as described in Example 14. It was then purified by adsorption onto PRP-1 reverse phase resin. The resin was washed With 1 ml of saline and 1 ml of 1:1 ethanol/saline, and then the complex was eluted with 0.4 ml of 95% ethanol. A 400 μl aliquot of pH 8.0 phosphate buffer (0.1M) was added and the mixture was heated at 37° C. for 30 minutes. During this time, the axial chloro ligand was replaced by a hydroxyl group in 96% yield as determined by HPLC. Samples of this complex co-eluted with authentic samples of $^{99}$Tc(OH)(dimethyl glyoxime)$_3$-1-(2-nitroimidazolyl)benzyl boron, prepared by treatment of the $^{99}$Tc-chloro complex with aqueous sodium hydroxide.

EXAMPLE 31

Preparation of $^{99m}$Tc(chlorine)(1,2-cyclohexanedionedioxime)$_3$-1-(propane-nitroimidazolyl)boron The title compound was prepared as described in Example 12, except that 3 mg of BpropNO$_2$(Example 20) was substituted for the 1-(2-nitroimidazolyl)-benzyl boronic acid. The yield of title complex, as determined by HPLC, was 95%.

EXAMPLE 32

Preparation of $^{99m}$Tc(chlorine)(1,2-cyclohexane-dionedioxime)$_3$-1-(propene-nitroimidazolyl)boron The title compound was prepared as described in Example 12, except that 3 mg of BpropenNO$_2$(Example 19) was substituted for the 1-(2-nitroimidazolyl)-benzyl boronic acid. The yield of title complex, as determined by HPLC, was 83%.

EXAMPLE 33

Preparation of (R)-1-Azabicyclo[2,2,2]oct-3-yl-(R)-α-(4)-Phenylboronic acid-α-phenylacetate (R)QN(R)B boronic acid)

This compound was prepared by the following reaction scheme:

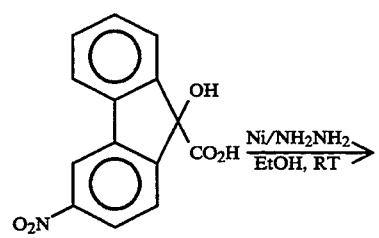

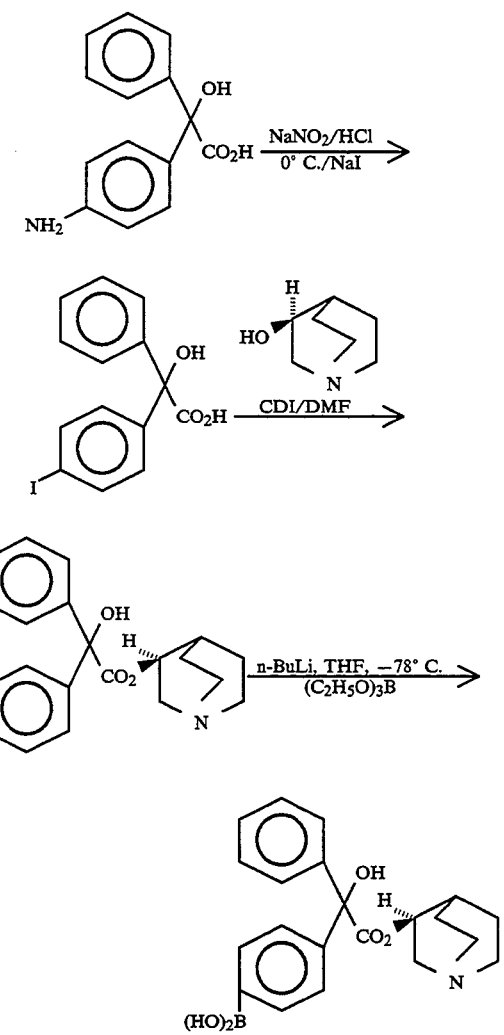

A. (RS)-3-Acetoxyquinuclidine

A solution of (RS)-3-quinuclidinol (25 g, 0.2 mmol) in pyridine (100 ml) was treated with acetic anhydride (100 ml), kept at 50° C. for 4 hours and left at room temperature for 15 hours. After removal of the pyridine and excess acetic anhydride under vacuum, the clear light brown oil was then dissolved in water (25 ml) and made slightly alkaline with saturated potassium carbonate. The ester was then extracted with chloroform (5×50 ml) and extracts were dried over K$_2$CO$_3$. After evaporation of the solvent in vacuo the residue was distilled yielding 20.6 g (62%) of (RS)-3-acetoxyquinuclidine as a colorless liquid.

$^1$HNMR (CDCl$_3$) δ1.31–2.01 (m, 6H), 2.11 (s, 3H, OCOCH$_3$), 2.62–2.95 (m, 5H), 3.18–3.31 (m, 1H), 4.80 (m, 1H, 3H).

B. (R)-(+)-3-Acetoxyquinuclidine (RS)-3-Acetoxyquinuclidine (34 g, 0.2 mmol) was added to a solution of L-(+)-tartaric acid (30.13 g, 0.2 mmol) dissolved in ethanol (80%, 142 ml). The solution was kept overnight at room temperature. The colorless crystalline solid (40 g) filtered and recrystallized twice from ethanol (80%, 280 ml) providing 25.5 g (65%) of resolved tartrate salt of (R)-(+)-3-acetoxyquinuclidine mp 96°–98° C. Rzeszotashi, *J. Med. Chem.*, mp 94°–95.5° C. The resolved tartrate salt of (R)-(+)-3- acetoxyquinuclidine (25.0 g) was dissolved in water (5 ml) and the solution made faintly alkaline with saturated $K_2CO_3$, and extracted with chloroform (5×25 ml). The combined $CHCl_3$ extracts were dried over anhydrous $Na_2SO_4$ and filtered. After evaporation of the solvent in vacuo the residue was distilled to provide (R)-(+)-3-acetoxyquinuclidine as a colorless liquid. Yield: 10.7 g (88%) $[\alpha]^D_{25}+29.96°$(c 2.93, ethanol). Lit. (Cohen et al. J. Pharm. Sci., (1989) 78 833–836 $[\alpha]^D_{25}+29.8°$(c 3 0 ethanol) $^1$HNMR ($CDCl_3$) δ1.30–2.01 (m, 6H), 2.13 (s, 3H, $OCOCH_3$), 2.62–2.98 (m, 5H), 3.18–3.30 (m, 1H), 4.82 (m, 1H, 3-H).

C. (R)-(+)-4-Nitrobenzilic acid

To a suspension of quinidine (39.6 g, 90%, 1.1 mmol) in boiling ethyl acetate (250 ml) was added the racemic (RS)-4-nitrobenzilic acid (30.0 g, 1.1 mmol) and kept at room temperature for 18 hours. The salt which crystallized was filtered, and after four recrystallizations from ethyl acetate had a constant melting point of 120°–122° C.; Yield 19.5 g (59.4%) TLC [silica gel, toluene-HOAc 9:1] $R_f$ 0.24.

The quinidine salt (1g, 1.68 mmol) was then treated with an excess of 6M hydrochloric acid and extracted with ethyl acetate. The extract was dried over anhydrous $MgSO_4$ and the solvent was removed under reduced pressure to afford a paste which was then loaded onto a silica gel (8 g) column and eluted with $CH_2Cl_2$-MeOH (95:5). The fractions with compound were pooled together and evaporated to a colorless paste which crystallized slowly to a cream colored solid. Yield: 0.35 g (77%) mp 104°–106° C. Thin layer chromatography [silica gel toluene-HOAc 9:1]Rf 0 3; $[\alpha]^D_{25}+50.11°$(c 1.34, acetone). Lit. (Rzeszotarski et al. J. Med. Chem., (1981), 27, 156–160), $[\alpha]^D24$ +49.4°(c 1.34, acetone).

$^1$HNMR ($CDCl_3$) δ4.80(bs, 2H, COOH and OH), 7.35 (m, 5H, $C_6H_5$), 7.71 and 8.21 (2d, 4H, $C_6H_4$).

D. (R)-4-Aminobenzilic acid

A solution of (R)-4-nitrobenzilic acid (2.0 g, 7.33 mmol) in ethanol (25 ml) was treated with hydrazine (1.0 ml) and Raney-Ni (0.8 g) and stirred at room temperature for 18 hours under a nitrogen atmosphere. The Raney-Ni powder was removed by filtration, washed with ethanol, the ethanol layer concentrated to a small volume and diluted with water (75 ml). The aqueous layer was extracted with ether (2×50 ml) and the aqueous layer was evaporated under vacuum to provide a light yellow solid of (R)-4-aminobenzilic acid in 82% yield (1.46 g); mp 139°–140° C. (decomp); TLC [silica gel, acetone] $R_f$0.20; $^1$NMR ($D_2O$) δ6.75 and 7.18 (2d, 4H, $C_6H_4$) and 7.31 (s, 5H, $C_6H_5$).

E. (R)-4-Iodobenzilic acid

The iodobenzilic acid was prepared by adding dropwise over 30 minutes a solution of sodium nitrite (1.7 g, 24.64 mmol) in water (10 ml) to a solution of (R)-4-aminobenzilic acid (3.0 g, 12.35 mmol) in 10% hydrochloric acid (100 ml) at −5° C. Stirring was continued for an additional 30 minutes at −5° C., then a solution of potassium iodide (4.09 g, 24.64 mmol) in water (10 ml) was added slowly. The reaction mixture was stirred at 0° C. for 1 hour, then at ambient temperature for 1 hour. The resultant mixture was extracted with ethyl acetate (3×75 ml), and the combined extracts were washed with aqueous sodium thiosulfate (10%, 2×50 ml), water (2×50 ml) and dried over sodium sulfate. Removal of solvent afforded a brown paste, which was purified by column chromatography (silica gel, eluted with ethanol/dichloromethane) to give the product as a light yellow solid. Yield 2.18 g (50%); mp 80°–81° C.; TLC [silica gel, toluene-acetic acid 9:1] $R_f$ 0.40; $[\alpha]^D25+24.7°$(c 0.132, acetone); $^1$H NMR ($CDCl_3$) δ5.50 (bs, 2H, COOH and OH), 7.21 and 7.69 (2d, 4H, $C_6H_4$) and 7.41 (s, 5H, $C_6H_5$).

F. (R)-3-Quinuclidinyl-(R)-4-iodobenzilate

A solution of (R)-4-iodobenzilic acid (0.26 g, 0.74 mmol) in dry dimethylformamide (2 ml) was treated with 1,1'-carbonyldiimidazole (0.12 g, 0.74 mmol) in small portions and stirred at room temperature for 1 hour under nitrogen atmosphere. To this light yellow colored solution, was added (R)-3-quinuclidinol (0.93 g, 0.73 mmol) and stirring was continued for an additional 15 hours at room temperature. The reaction mixture was concentrated under vacuum and added to water (50 ml) and extracted with ether (3×30 ml). The combined ether extracts were washed with saturated sodium bicarbonate (2×20 ml), water (2×20 ml) and dried over anhydrous sodium sulfate. To the paste thus obtained was added silica gel (0.5 g), ether (5 ml) and the mixture was dried. The dry silica gel powder with compound was loaded onto a silica gel column (10 g) and eluted with 5% methanol in dichloromethane solvent mixture. The fractions with compound were pooled together and evaporated on a rotary evaporator to afford a light yellow solid in 75% yield (0.256 g); mp 124°–127° C.; TLC[silica gel, MeOH-$NH_4OH$ 98:2] $R_f$0.65; $^1$HNMR ($CDCl_3$)δ1.15–1.89 (m, 4H), 2.01 (s, 1H) 2.42–2.81 (m, 5H), 3.21 (m, 1H), 4.52 (bs, 1H, OH), 5.01 (m, 1H), 5.01 (m, 1H) and 7.15–7.82 (m, 9H, Ar-H).

G. (R)QN(R)B boronic acid

To a solution of (R)-3-quinuclidinyl-(R)-4-iodobenzilate (0.60 g, 1.3 mmol) in freshly distilled tetrahydrofuran (2.0 ml) in a dry 10 ml round bottom flask at −78° C. was added via syringe n-BuL1 (0.2 g, 2.5 M, 1.25 ml, 3.13 mmol) slowly and stirred at the same temperature for 20 minutes. Then freshly distilled triethyl borate (0.378 g, 0.441 ml, 2.59 mmol) was added to this reaction mixture and stirred for an additional 1 hour at −78° C., allowed to raise its temperature to ambient condition, and stirred for 18 hours. The reaction mixture was then treated with a few drops of water, decanted to remove solution phase from the semi-solid, and the solid then repeatedly washed with ether and finally triturated with ether to give a colorless solid. The solid was dissolved in water containing <5% acetonitrile, filtered and loaded onto a reverse phase $C_{18}$ HPLC column (Dynamax $C_{18}$, 4.14×25 cm, 8 micron) and eluted under isocratic conditions with 12.5% acetonitrile containing 0.1% trifluoroacetic acid/$H_2O$. The fractions were checked via analytical HPLC (Dynamax $C_{18}$, 0.46×25 cm, 8 micron, 18% acetonitrile with 0.1% trifluoroacetic acid in 0.1% trifluoroacetic acid/water) and the fractions with the title compound in >98% purity were pooled, and freeze-dried to afford (R)QN(R)B boronic acid as a colorless solid in trifluoroacetic acid salt form; yield: 0.025 g (4.4%); $^1$NMR ($CD_3OD$) 6 1.68 (m H I 2H) 1.95 (m 2H), 2.35 (s, 1H), 2.81–3.35 (m, 5H), 3.80 (m, 1H), 5.31 (m, 1H) and 7.28–7.71 (m, 9H, Ar-H). MS: Exact Mass calculated for $C_{24}H_{29}O_6NB$: 438.2092; experimental, 438.2088.

EXAMPLE 34

Preparation of (S)-1-Azabicyclo[2,2,2]oct-3-yl-(R)-α-Hydroxy-α-(4)-Phenylboronic acid-α-phenylacetate (S)QN(R)B boronic acid)

This compound was prepared by the reaction scheme outline in Example 33, substituting S-quinuclidinol for R-quinuclidinol.

A. (S)-3-acetoxyquinuclidine

The mother liquors from Example 33A (preparation of (R)-3-acetoxyquinuclidine), were concentrated in vacuo and the residue was made alkaline with potassium carbonate. The ester was extracted with chloroform (3×50 ml) and dried with sodium sulfate. The solvent was evaporated yielding 7.5g of the crude ester. The ester was added to a solution of (−)-tartaric acid (6.5 g in 80% ethanol) and the salt formed was purified as described in Example 33A. mp. 95°–96° C. lit(Cohen et al. J. Pharm. Sci., (1989), 78, 833–836) mp 94°–96° C.

B. (S)-3-Quinuclidinyl-(R)-4-iodobenzilate

The title compound was prepared as a colorless paste in 73% yield (0.25 g) from (R)-4-iodobenzilic acid (0.26 g, 0.73 mmol), 1,1'-carbonyldiimidazole (0.12 g, 0.74 mmol) and (R)-3-quinuclidinol (0.93 g, 0.73 mmol) in dry dimethylformamide (2 ml) as described for the synthesis of (R)-3-quinuclidinyl-(R)-4-iodobenzilate (Example 33); TLC [silica gel, MeOH-NH$_4$OH 98:2]R$_f$ 0.69; $^1$H NMR (CDCl3) δ1.15–1.89 (m, 4H), 2.01 (s, 1H), 2.42–2.81 (m, 5H), 3.21 (m, 1H), 4.52 (bs, 1H, OH), 5.01 (m, 1H), 5.01 (m, 1H) and 7.15–7.82 (m, 9H, Ar-H).

C. (S)-1-Azabicyclo[2,2,2]oct-3-yl-(R)-α-Hydroxy-α-(4)-Phenylboronic acid-α-phenylacetate ((S)QN(R)B boronic acid)

This compound was synthesized as a colorless solid (TFA salt form) in 11% yield (58 mg) from (S)-3-quinuclidinyl-(R)-4-iodobenzilate (0.6 g, 1.3 mmol), n-BuLi (0.2 g, 2.5 M, 1.25 ml, 3.13 mmol) and triethyl borate (0.378 g, 0.441 ml, 2.59 mmol) in dry tetrahydrofuran at −78° C. as described for the synthesis of (R)QN(R)B boronic acid (Example 33); $^1$HNMR (CD$_3$OD) δ1.68(m, 2H), 1.95(m, 2H), 2.35(s, 1H), 2.81–3.35(m, 5H), 3.80 (m, 1H), 5.31(m, 1H)) and 7.28–7.71 (m, 9H, Ar-H). MS: Exact Mass calculated for C$_{24}$H$_{29}$O$_6$NB: 438.2092; experimental, 438.1190.

EXAMPLE 35

Preparation of (S)-1-Azabicyclo[2,2,2]oct-3-yl-(S)-α-Hydroxy-α-(4)-Phenylboronic acid-α-phenylacetate((S)QN(S)B boronic acid)

This compound was prepared by the following reaction scheme:

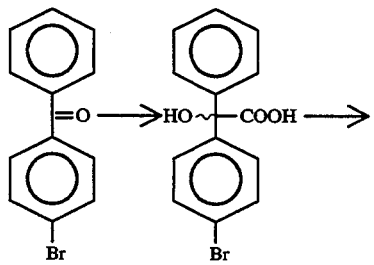

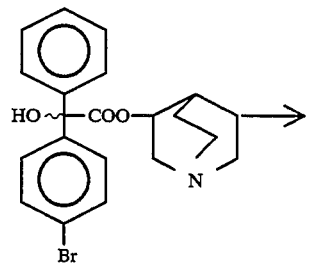

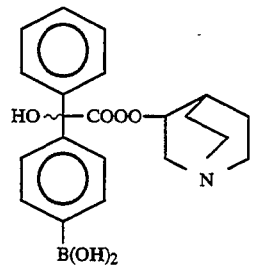

A. (RS)-4-Bromobenzilic acid

Zinc iodide (0.5 g) was added to a stirring solution of 4-bromobenzophenone (54.81 g, 0.21 mol) in dry dichloromethane (500 ml) at room temperature under N$_2$ atmosphere. Trimethylsilyl cyanide (25 g, 0.25 mol) was added dropwise from an addition flask over a period of 1 hour and the mixture stirred at room temperature for 72 hours. The reaction mixture was treated with saturated sodium bicarbonate (200 ml) and stirred for 1 hour. The organic layer was separated, washed with water (2×150 ml) and concentrated. The residue was suspended in H$_2$O:HCl:AcOH (1:33; 500 ml) and heated at 85°–90° C. for 48 hours. The solution was concentrated under vacuum to about 100 ml and treated with saturated sodium bicarbonate (400 ml) and extracted with ether (3×100 ml). The aqueous layer was acidified with 6N hydrochloric acid and the separated solid was dissolved in ether (300 ml). This organic layer was washed with water, filtered and the filtrate was evaporated to provide a colorless crystalline solid of (RS)-4-bromobenzilic acid in 19% yield (12 g); mp 125°–126° C.; TLC [silica gel, toluene-acetic acid] R$_f$ 0.32; $^1$H NMR (DMSO-d$_6$) δ2.38 (bs, 2H, COOH and OH) and 7.38–7.70 (m, 9H, AR-H).

B. 3-S-Quinuclidinyl 4'-bromobenzilate

N,N'-Carbonyldiimidazole (0.810 g, 0.005 mol) was added to solution of racemic p-bromobenzilic acid (1.53 g, 0.005 mol) in dimethylformamide (5 ml) under nitrogen atmosphere and the mixture was stirred for 1 hour at 40° C. s-Quinuclidinol (0.8 g, 0.0063 mol) was added and the mixture was stirred at 40° C. for 24 hours. Workup afforded 1.12 g of 3-S-quinuclidinyl 4'-bromobenzilate. mp. 151°–53° C. $^1$HNMR (DMSO-d$_6$) δ1.3–3.3 (m, Quinuclidinyl protons), 4.9 (m, 1H, CHO), 7.3–7.7 (m,9H,ArH). MS: (2M+H)+=416+ and 418+.

C. (S)-1-Azabicyclo[2,2,2]oct-3-yl-(S)-α-Hydroxy-α-(4)-Phenylboronic acid-α-phenylacetate To a cooled (−78° C.) solution of 3-S-quinuclidinyl 4'-bromobenzilate (417 mg, 0.001 mol) in dry tetrahydrofuran (30 ml) was added n-BuLi (2.5 M solution in hexane, 1.0 ml, 0.165 g, 0.0025 mol) via a syringe. The mixture was stirred for 1 hour at −78° C. and triethylborate (2 ml) was added at −78° C. The mixture was stirred for an additional 1 hour at −78° C. and 4 hours at room temperature. Tetrahydrofuran was removed and the residue was treated with water and extracted with ethyl acetate and dried with sodium sulfate. The solvent was evaporated to yield a semisolid which was triturated with ether to give 100 mg of 25 (S)QN(RS)B-boronic acid. mp 212°–215° C. (decomp). The S,S stereoisomer was isolated from this mixture of diastereoisomers by preparative HPLC, as described in Example 33G. $^1$H NMR of the S,S-stereoisomer (D$_2$O): δ1.40–1.70 (m, 2H), 1.17–3.03 (m, 2H), 2.32 (s, 1H), 2.65–2.85 (m, 1H), 3.00–3.22 (m, 4H), 3.60 (m, 1H), 5.28 (m, 1H), 7.35 (m, 7H), 7.72 (d, 2H).

EXAMPLE 36

Preparation of (R)-1-Azabicyclo[2,2,2]oct-3-yl-(S)-α-(4)-Phenylboronic acid-α-phenylacetate (R)QN(S)B boronic acid)

This compound was prepared by the reaction scheme shown in Example 35.

A. 3-R-Quinuclidinyl 4'-bromobenzilate

N,N'-Carbonyldiimidazole (0.810g, 0.005 mmol) was added to a solution of p-bromobenzilic acid (Example 35A, 1.53 g, 0.005 mmol) in dimethylformamide (5 ml) under nitrogen and the mixture was stirred for 1 hour at 40° C. R-Quinuclidinol (0.8 g, 0.0063 mol) was added and the mixture was stirred at 40° C. for 24 hours. Dimethylformamide was removed under vacuum and the residue was poured into water. The precipitated solid was filtered and air dried. Yield 1.2 g (58%). $^1$H NMR (DMSO-d$_6$) δ1.3–3.3 (m, Quinuclidinyl protons), 4.9 (m, 1H, CHO), 7.3–7.7 (m, 9H, ArH). MS (2M−H)+ =416+ and 418+.

B. (R)-1-Azabicyclo[2,2,2]oct-3-yl-(S)-α-Hydroxy-α-(4)-Phenylboronic acid-α-phenylacetate ((R)QN(S)B boronic acid)

To a cooled (−78° C.) solution of 3-quinuclidinyl 4'-bromobenzilate (316 mg, 0.00076 mol) in dry tetrahydrofuran (30 ml) was added n-BuLi (2.5 M solution in hexane, 0.72 ml, 0.12, 0.0018 mol) via a syringe. The mixture was stirred for 1 hour at −78° C. and triethylborate (1 ml) was added at −78° C. The mixture was stirred for an additional 1 hour at −78° C. and 4 hours at room temperature. Tetrahydrofuran was removed and the residue was treated with water and extracted with ethyl acetate and dried with sodium sulfate. The solvent was evaporated to yield a semisolid which was triturated with ether to give a solid. Yield 50 mg. The S,R stereoisomer was isolated from this mixture of diastereoisomers by preparative HPLC, as described in Example 33G. mp 213°–215° C. (decomp). $^1$H NMR (D$_2$O) δ1.41–1.70 (m, 2H), 1.71–2.02 (m, 2H), 2.32 (s, 1H), 2.65–2.85 (m, 1H), 3.00–3.22 (m, 4H), 3.60 (m, 1H), 5.28 (m, 1H), 7.35 (m, 7H), 7.72 (d, 2H).

EXAMPLE 37

Preparation of $^{99m}$TcCl(DMG)$_3$[(RR or RS)QNB boron]

Into a 5 ml siliconized serum vial were measured 2.0 mg of dimethyl glyoxime, 1.5 mg of 3-R-quinuclidinyl-(4-borono-R-benzilate) [(R)QN(R)B-boronic acid] or 3-R-quinuclidinyl-(4-borono-S-benzilate) [(S)QN(R)B-boronic acid], 20 mg of citric acid, 100 mg of NaCl, 2.0 mg of diethylenetriaminepenta-acetic acid, and 125 µg of SnCl$_2$ (in 4 M HCl) in a total volume 0.7 ml of 28% ethanol/saline. 0.5 ml of $^{99m}$TcO$_4$-generator eluent was added and the mixture was heated at 70° C. for 15 minutes, yielding 60–70% of the desired compound as determined by HPLC. Chromatographic purification of the reaction mixture on PRP-1 resin yielded the product in >90% purity.

EXAMPLE 38

Preparation of $^{99m}$TcCl(CDO)$_3$(QNB-boron)

Into a 5 ml siliconized serum vial were measured 2.0 mg of 1,2-cyclohexanedione dioxime, 1.5 mg of 3-quinuclidinyl-(4-borono-benzilate) (QNB-boronic acid), 20 mg of citric acid, 100 mg of NaCl, 2.0 mg of diethylenetriaminepenta-acetic acid, and 125 µg of SnCl$_2$ (in 4M HCl) in a total volume 0.7 ml of 28% ethanol/saline. 0.5 ml of $^{99m}$TcO$_4$-generator eluent was added and the mixture was heated at 70° C. for 15 minutes, yielding 83% of the desired compound as determined by HPLC. Chromatographic purification of the reaction mixture on PRP-1 resin yielded the product in >90% purity.

STRUCTURES OF BORONIC ACIDS IN THE EXAMPLES

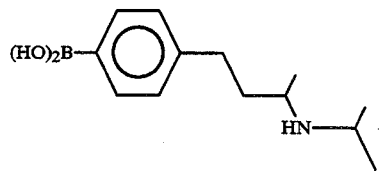

Examples 1 and 2

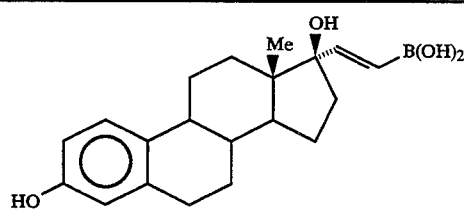

Estradiol boronic acid (examples 4–7)

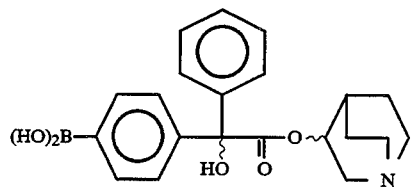

QNB-boronic acid (examples 8, 9, 33–36)

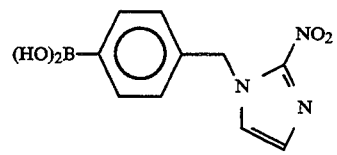

BBNO$_2$ (example 10)

STRUCTURES OF BORONIC ACIDS IN THE EXAMPLES

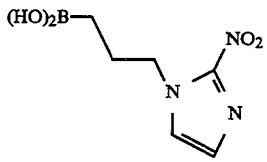

BpropNO$_2$ (example 20)

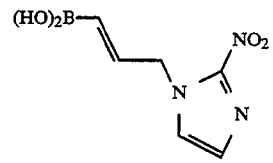

BpropenNO$_2$ (example 19)

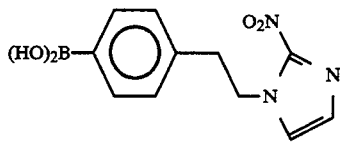

BPhEtNO$_2$ (example 11)

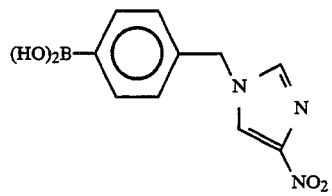

BB4NO$_2$ (example 21)

What is claimed:

1. A boronic acid adduct of technetium dioxime or rhenium dioxime complexes having the formula

MX(Y$_3$)Z wherein M is a radionuclide of technetium or rhenium; X is an anion; Y is a vicinal dioxime having the formula $$\overset{R_1}{\underset{|}{HO-N=C}}-\overset{R_2}{\underset{|}{C=N-OH}}$$

or a pharmaceutically acceptable salt thereof,
wherein R$_1$ and R$_2$ are each independently hydrogen, halogen, alkyl, aryl, amino or a 5- or 6-membered nitrogen or oxygen containing heterocycle, or together R$_1$ and R$_2$ are —(CR$_8$R$_9$)$_n$— wherein n is 3, 4, 5 or 6 and R$_8$ and R$_9$ are each independently hydrogen or alkyl; and Z is a boron derivative of the formula B—(A$_1$)$_p$—R$_3$ wherein R$_3$ is, or contains, a biochemically active group selected from the group consisting of hypoxia-mediated nitro-heterocyclic groups, steroids or molecules with an affinity for a steroid receptor site, sugars, barbiturates, monoamine oxidase substrates and inhibitors, antihypertensives, substrates for muscarinic receptors and substrates for dopamine receptors, and wherein (A$_1$)$_p$ is absent when p is zero or is a spacer group when p is an integer ≧one, wherein, when p is an integer greater than zero, the various A$_1$ units (which form a straight or branched chain) are independently selected from —CH$_2$—, —CHR$_4$—, —CR$_4$R$_5$—, —CH=CH—, —CH=CR$_4$—, —CR$_4$=CR$_5$—, —C≡C—, cycloalkyl, cycloalkenyl, aryl, heterocyclo, oxygen, sulfur,

—NH—, —HC=N—, —CR$_4$=N—, —NR$_4$—, or —CS—, in which R$_4$ and R$_5$ are independently selected from alkyl, alkenyl, alkoxy, aryl, 5- or 6-membered nitrogen or oxygen containing heterocycle, halogen, hydroxy or hydroxyalkyl.

2. The boronic acid adduct of claim 1 wherein said biochemically active group at R$_3$ is a metabolic substrate or inhibitor, or a molecule with an affinity for a specific receptor.

3. The boronic acid adduct of claim 1 containing the spacer (A$_1$)$_p$ wherein p is an integer greater than zero, and the various A$_1$ units (which form a straight or branched chain) are independently selected from —CH$_2$—, —CHR$_4$—, —CR$_4$R$_5$—, —CH=CH—, —CH=CR$_5$—, —CR≡C—, cycloalkyl, cycloalkenyl, aryl, heterocyclo, oxygen, sulfur,

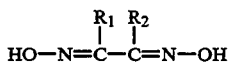

—NH—, —HC=N—, —CR$_4$=N—, —NR$_4$—, —CS—; wherein R$_4$ and R$_5$ are independently selected from alkyl, alkenyl, alkoxy, aryl, 5- or 6-membered nitrogen or oxygen containing heterocycle, halogen, hydroxy or hydroxyalkyl.

4. The boronic acid adduct of claim 1 wherein (A$_1$)$_p$ is absent or is selected from alkyl, oxa-alkyl, hydroxyalkyl, hydroxyalkoxy, alkenyl arylalkyl, alkenyl, arylalkylamide, alkylamide, alkylamine and (alkylamine)alkyl.

5. The boronic acid adduct of claim 1 wherein (A$_1$)$_p$ is absent or is selected from —(CH$_2$)$_{2-3}$—, —CH$_2$—CH=CH—CH$_2$—,

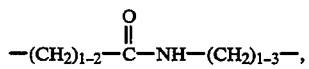

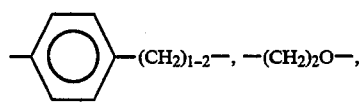

—CH$_2$CH(OH)CH$_2$OCH$_2$—,

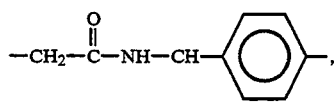

—(A$_3$—O—A$_3'$)$_{1-3}$—, —(A$_3$—NH—A$_3'$)$_{1-3}$— or —CH$_2$CH=CH—;

wherein A$_3$ and A$_3'$ are the same or different alkyl.

6. A boronic acid adduct in accordance with claim 1 wherein X is a halide.

7. A boronic acid adduct in accordance with claim 6 wherein X is chloride or bromide.

8. A boronic acid adduct in accordance with claim 7 wherein X is chloride.

9. A boronic acid adduct in accordance with claim 1 wherein X is hydroxy.

10. A boronic acid adduct in accordance with claim 1 wherein Y is dimethylglyoxime, 1,2-cyclohexanedione dioxime, 1,2-cyclopentanedione dioxime, or 3-methyl-1,2-cyclopentanedione dioxime.

11. A boronic acid adduct in accordance with claim 1 wherein $R_3$ is asteroid.

12. A boronic acid adduct in accordance with claim 11 wherein $R_3$ is estradiol, [17α(E)-3,17-dihydroxy-1,3,5(10)-estratrien-17-yl]ethenyl.

13. A boronic acid adduct in accordance with claim 12 wherein $R_3$ is MIVE, [[11-β, 17-α(E)]-3,17-dihydroxy-11-methoxy-1,3,5(10)-estratrien-17-yl]ethenyl.

14. A boronic acid adduct in accordance with claim 1 wherein $R_3$ is a substrate for a muscarinic receptor.

15. A boronic acid adduct of claim 14 wherein $R_3$ is 3-quinuclidinyl benzilate.

16. A boronic acid adduct in accordance with claim 1 wherein $R_3$ is a hypoxia-mediated nitro-heterocyclic group.

17. A boronic acid adduct in accordance with claim 16 wherein $R_3$ is a hypoxia-mediated nitro-heterocyclic group and the spacer-$R_3$ portion of the complex are selected from

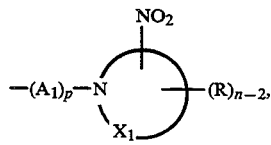

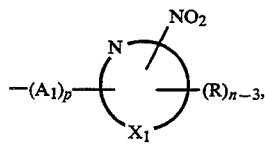

or

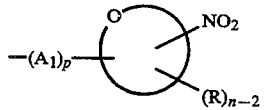

the ring portion being a 5- or 6-membered cyclic or aromatic ring, wherein;

n is the total number of substitution positions available on the 5- or 6-membered ring;

said one or more R groups are independently hydrogen, halogen, alkyl, aryl, alkoxy, oxa-alkyl, hydroxyalkoxy, alkenyl, arylalkyl, arylalkylamide, alkylamide, alkylamine and (alkylamine)alkyl;

$X_1$ is nitrogen, sulfur, oxygen, —CR= or —CRR—; and $(A_1)_p$ can be absent in which case the $R_3$ group is linked to the rest of the adduct of claim 1 via a nitrogen or carbon atom, or $(A_1)_p$ comprises the link between $R_3$ and said rest of the adduct of claim 1.

18. The boronic acid adduct of claim 17 wherein said hypoxia-mediated nitro-heterocyclic group is selected from 2-, 4- or 5-nitroimidazoles, nitrofurans, nitrothiazoles and derivatives thereof.

19. A compound according to claim 1 having the name Tc(chloride)(dimethylglyoxime)$_3$(estradiol boron).

20. A compound according to claim 1 having the name TcCl(cyclohexanedionedioxime)$_3$(estradiol boron).

21. A compound according to claim 1 having the name [TcCl(dimethylglyoxime)$_3$[3-quinuclidinyl(4-boronobenzilate)]].

22. A compound according to claim 1 having the name Tc(chlorine)(1,2-cyclohexanedionedioxime)$_3$1-(2-nitroimidazoyl)benzylboron.

23. A compound according to claim 1 having the name Tc(chlorine)(dimethylglyoxime)$_3$1-(2-nitroimidazoyl)benzylboron.

24. A compound according to claim 1 having the name Tc(chlorine)(dimethylglyoxime)$_3$-4-(2-nitroimidazole ethyl)phenyl boron.

25. A compound according to claim 1 having the name Tc(chlorine)(dimethylglyoxime)$_3$-1-(n-propyl-2-nitroimidazolyl)boron.

26. A compound according to claim 1 having the name Tc(chlorine)(dimethylglyoxime)$_3$-1-(propene-2-nitroimidazolyl)boron.

27. A compound according to claim 1 having the name Tc(chlorine)(dimethylglyoxime)$_3$-1-(4-nitroimidazolyl) benzylboron.

28. A compound according to claim 1 having the name Tc(chlorine)(1,2-cyclohexane-dionedioxime)$_3$-1-(4-nitroimidazolyl)benzylboron.

29. A compound according to claim 1 having the name Tc(hydroxy)dimethylglyoxime)$_3$-1-(2nitroimidazolyl)benzylboron.

30. A compound according to claim 1 having the name Tc(chlorine)(1,2-cyclohexane-dionedioxime)$_3$-1-(propane-nitroimidazolyl)boron.

31. A compound according to claim 1 having the name Tc(chlorine)(1,2-cyclohexane-dionedioxime)$_3$-1-(propene-nitroimidazolyl)boron.

32. A kit suitable for labelling with a radionuclide of technetium or rhenium, said kit comprising:

(i) a source of anion;

(ii) a boronic acid derivative, (or compounds which can react in situ to form a boronic acid derivative) having the formula

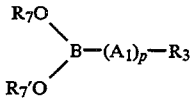

or a pharmaceutically acceptable salt thereof, wherein $R_7$ and $R_7'$ are each independently hydrogen, alkyl, or aryl, or where $R_7$ and $R_7'$ taken together are —$(CR_8R_9)_{2-6}$— and $R_8$ and $R_9$ are independently hydrogen or alkyl; and wherein $R_3$ is or contains a biochemically active group selected from the group consisting of hypoxia-mediated nitro-heterocyclic groups, steroids, sugars, barbiturates, monoamine oxidase substrates and inhibitors, antihypertensives, substrates for muscarinic receptors and substrates for dopamine receptors;

and wherein $(A_1)_p$ is absent or is a spacer group, wherein, when p is an integer greater than zero, the various $A_1$ units (which form a straight or branched chain) are independently selected from —CH$_2$—, —CHR$_4$—, —CR$_4$R$_5$—, —H=CH=, —CH=CR$_4$—, —CR$_4$=CR$_5$—, —C≡C—, cycloalkyl, cycloalkeny, aryl, heterocyclo, oxygen, sulfur,

—NH—, —HC=N—, —CR$_4$=N—, —NR$_4$—, or —CS—, in which R$_4$ and R$_5$ are independently selected from alkyl, alkenyl, alkoxy, aryl, 5- or 6-membered nitrogen or oxygen containing heterocycle, halogen, hydroxy or hydroxyalkyl;

(iii) a dioxime having the formula

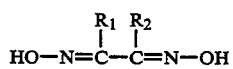

or a pharmaceutically acceptable salt thereof,
wherein R$_1$ and R$_2$ are each independently hydrogen, halogen, alkyl, aryl, amino or a 5- or 6-membered nitrogen or oxygen containing heterocycle, or together R$_1$ and R$_2$ are —(CR$_8$R$_9$)$_n$— wherein n is 3, 4, 5 or 6 and R$_8$ and R$_9$ are each independently hydrogen or alkyl; and, (iv) a reducing agent.

33. A kit in accordance with claim 32 wherein the source of anion is a source of halide.

34. A kit in accordance with claim 32 wherein the source of anion is chloride or bromide.

35. A kit in accordance with claim 32 wherein the dioxime is dimethylglyoxime, 1,2-cyclohexanedione dioxime, 1,2-cyclopentanedione dioxime, or 3-methyl-1,2-cyclopentanedione dioxime.

36. A kit in accordance with claim 32 wherein the reducing agent is a stannous salt.

37. A kit in accordance with claim 32 wherein said biochemically active group is a metabolic substrate or inhibitor, or a molecule with an affinity for a receptor site.

38. A kit in accordance with claim 32 wherein R$_3$ is asteroid.

39. A kit in accordance with claim 32 wherein R$_3$ is estradiol, [17α(E)-3,17-dihydroxy-1,3,5(10)-estratrien-17-yl]ethenyl.

40. A kit in accordance with claim 32 wherein R$_3$ is MIVE, [[11-β, 17-α(E)]-3,17-dihydroxy-11-methoxy-1,3,5(10)-estratrien-17-yl]ethenyl.

41. A kit in accordance with claim 32 wherein R$_3$ is a substrate for a muscarinic receptor.

42. A kit in accordance with claim 32 wherein R$_3$ is 3-quinuclidinyl benzilate.

43. A method for the diagnostic imaging of hypoxic tissue in a mammalian species comprising the administration of a complex of formula I in claim 1 wherein M is technetium-99m and R$_3$ is or contains a hypoxia-mediated nitro-heterocyclic group.

44. A method for providing radiotherapy to a mammalian species in need thereof comprising the administration of a complex of formula I in claim 1 wherein M is a radionuclide of rhenium and wherein R$_3$ is or contains a hypoxia-mediated nitro-heterocyclic group or is selected from estrogen, estradiols and derivatives thereof.

45. A method for the diagnostic imaging of the heart in a mammalian species comprising the administration of a complex of formula I in claim 1 wherein M is technetium-99m and R$_3$ is or contains a biochemically active group selected from sugars and substrates for muscarinic receptors.

46. A method for the diagnostic imaging of the brain in a mammalian species comprising the administration of a complex of formula I in claim 1 wherein M is technetium-99m and R$_3$ is or contains a biochemically active group selected from substrates for muscarinic receptors and sugars and amphetamines.

47. A method for the diagnostic imaging of carcinoma in a mammalian species comprising the administration of a complex of formula I in claim 1 wherein M is technetium-99m and R$_3$ is or contains a hypoxia-mediated nitro-heterocyclic group, a sugar, or asteroid or molecule with an affinity for asteroid receptor site.

48. A method for the diagnostic imaging of estrogen receptor sites in a mammalian species in need thereof comprising the administration of a complex of formula I in claim 1 wherein M is technetium-99m and R$_3$ is selected from estrogen, estradiols and estradiol derivatives.

49. The method of claim 48 wherein the estrogen receptor site is selected from breast and uterine carcinoma.

50. A compound according to claim 1 having the name $^{99m}$TcCl(DMG)$_3$[(RR or RS)QNB boron].

51. A compound according to claim 1 having the name $^{99m}$TcCl(CDO)$_3$(QNB-boron).

* * * * *